United States Patent [19]

Ohyama et al.

[11] Patent Number: 5,221,959
[45] Date of Patent: Jun. 22, 1993

[54] COLOR DISCRIMINATION DATA INPUT APPARATUS

[75] Inventors: Nagaaki Ohyama, Kawasaki; Susumu Kikuchi, Hachioji; Takeshi Mori, Machida, all of Japan

[73] Assignee: Olympus Optical Co., Ltd., Tokyo, Japan

[21] Appl. No.: 667,969

[22] Filed: Mar. 12, 1991

[30] Foreign Application Priority Data

Mar. 16, 1990 [JP] Japan .................................. 2-65861
Feb. 5, 1991 [JP] Japan .................................. 3-14561

[51] Int. Cl.$^5$ .......................... G01J 3/28; G01N 21/25
[52] U.S. Cl. ................................... 356/326; 356/310; 356/330; 356/328; 356/416; 356/419; 364/526
[58] Field of Search ............................ 356/326-328, 356/402-411, 330-331, 310, 416, 419; 364/498, 526

[56] References Cited

U.S. PATENT DOCUMENTS 4,193.691 3/1980 Fjarlie .................................. 356/330
4,790,654 12/1988 Clarke .................................. 356/326

OTHER PUBLICATIONS

Article entitled "Color Recognition Systems" By Timo Jaaskelainen, published in the *Japanese Journal of Optics*, vol. 18, 1989.
Article entitled An Optimal Set of Discriminant Vectors By Donald H. Foley, et al, published in *IEEE Transactions on Computers*, vol. C-24, No. 3, Mar. 1975, pp. 281-289.
Article entitled Optical Implementation Of The Hotelling Trace Criterion For Image Classification By Zu-Han Gu, et al, published in *Optical Engineering*, vol. 23, No. 6, Nov.-Dec. 1984, pp. 727-731.
Article entitled Color Representation Using Statistical Pattern Recognition, J. Parkkinen, et al, published *Applied Optics*, vol. 26, No. 19, Oct. 1, 1987, pp. 4240-4245.
Article entitled "Color Recognition Systems" By Timo Jaaskelainen, published in *Laboratory of Applied Physics, Faculty of Engineering*, Saitama University and received Aug. 30, 1988.

*Primary Examiner*—F. L. Evans
*Assistant Examiner*—K. P. Hantis
*Attorney, Agent, or Firm*—Frishauf, Holtz, Goodman & Woodward

[57] ABSTRACT

A color discrimination data input apparatus includes a light source for generating illumination light for illuminating a target object, a spectroscope for producing a spectrum having a plurality of spectral components, a color classification filter set to have a light-transmitting characteristic to pass only a light component having a wavelength range suitable for classification from the spectral components generated by the spectroscope in order to classify the spectral components reflected by the target object into predetermined classes, a photoelectric converting circuit for converting a reflected spectral component, upon radiation of the spectral component passing through the color classification filter on the target object, into an electrical signal, classifying circuit for classifying the reflected spectral components in accordance with the electrical signal output from the photoelectric converting circuit, the color estimating circuit of estimating a color of the target object from the reflected spectral component classified into any one of the classes by the classifying circuit on the basis of a preset absolute color estimation matrix, and an output unit for outputting a classification result obtained from the classifying circuit and an object color measurement result output from the color estimating circuit.

15 Claims, 17 Drawing Sheets

FIG. 9A $\phi_1$
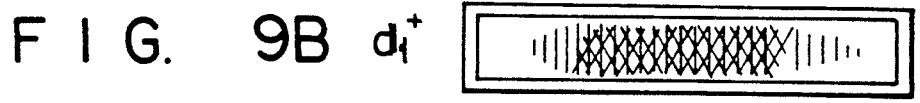
FIG. 9B $d_1^+$
FIG. 9C $d_1^-$
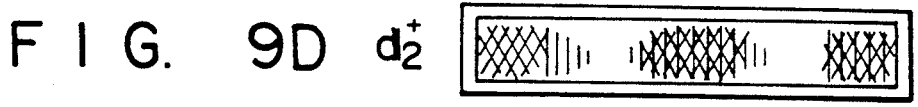
FIG. 9D $d_2^+$
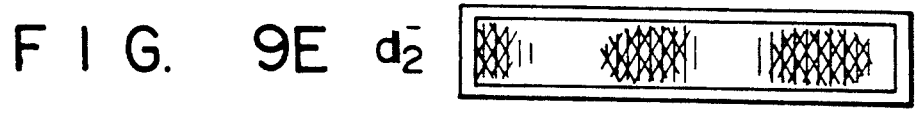
FIG. 9E $d_2^-$
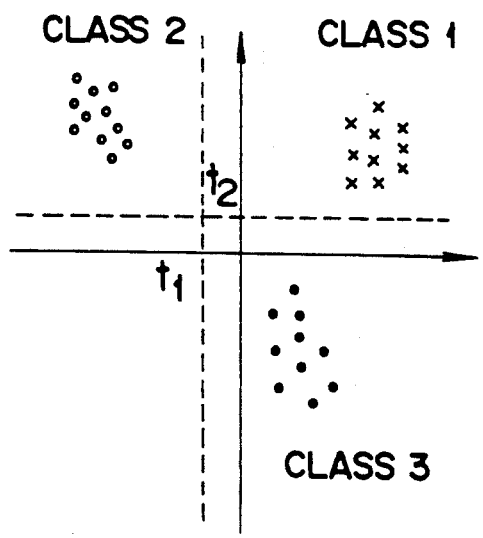
FIG. 10

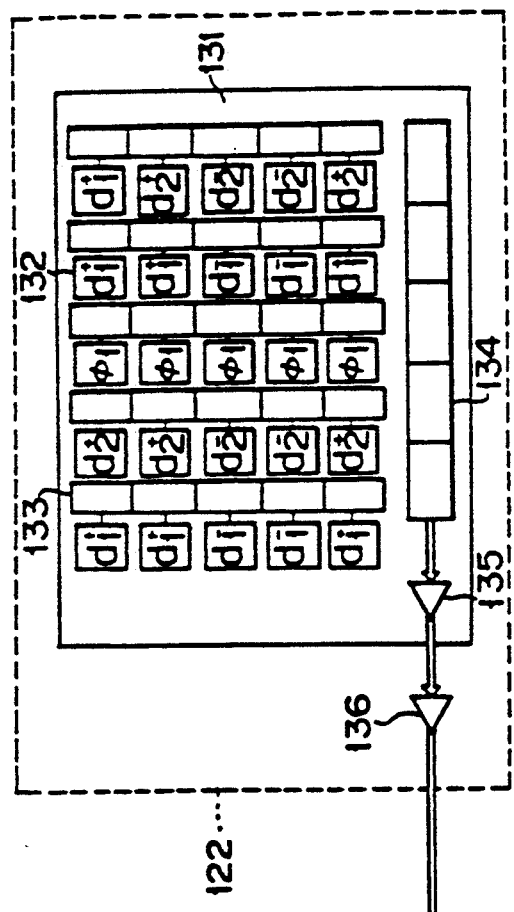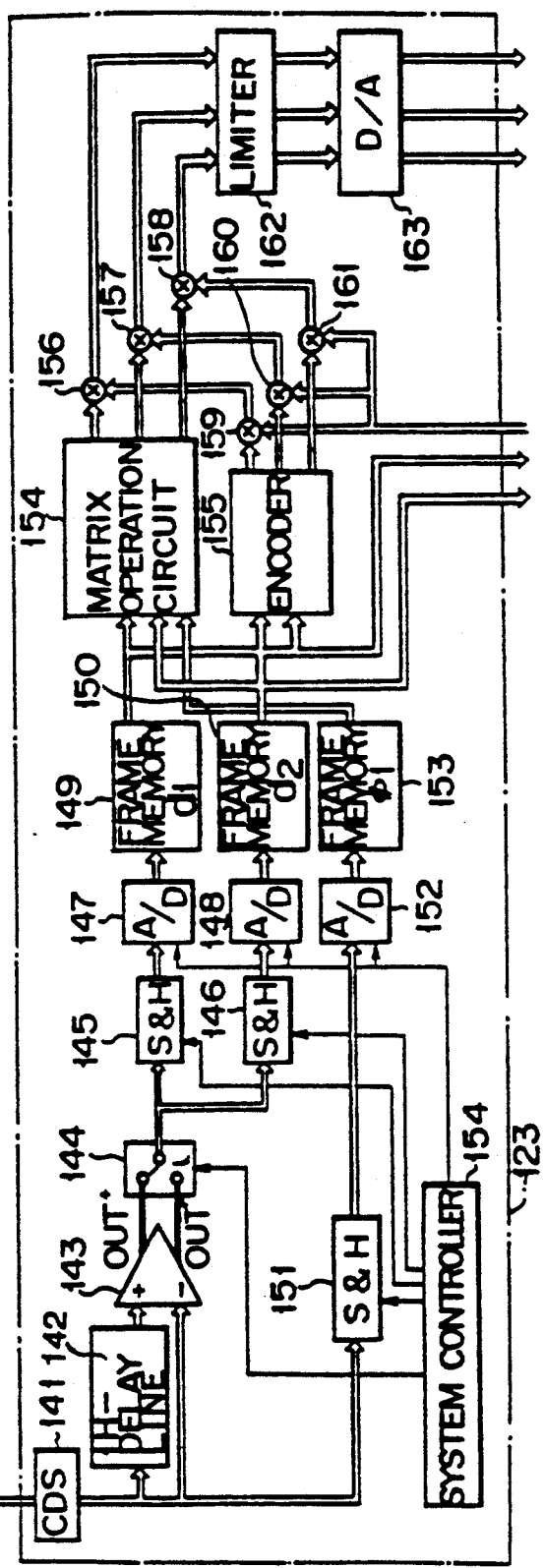
FIG. 18

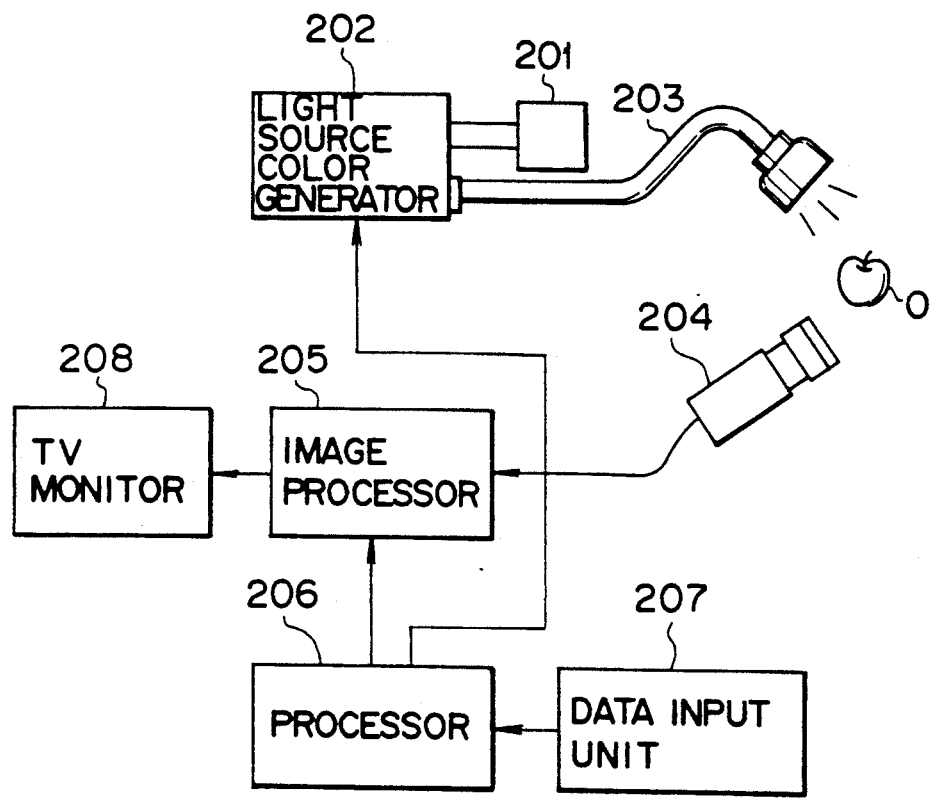
F I G. 19

COLOR DISCRIMINATION DATA INPUT APPARATUS

BACKGROUND OF THE INVENTION

1. Field of the Invention

The present invention relates to a color discrimination data input apparatus utilized in a variety of fields requiring detection of color information of an object, as in administration of dyeing colors and painting colors, color measurements of products, color classification, and color measurements in the fields of medical and scientific applications.

2. Description of the Related Art

A conventional color measuring apparatus measures intensities of reflected light in wavelength regions including three primary colors, i.e., red (R), green (G), and blue (B) from reflected light spectra obtained by spectrally analyzing light reflected by a target object, and converts the measured data into numeric values in accordance with a chromaticity chart as of an XYZ display color system standardized by the Commission Internationale de l'Echairage (CIE) or the International Commission on Illumination, and represents colors by these numeric values.

In a conventional general color image input/output apparatus, image data of R, G, and B, or cyan, magenta, and yellow as complementary colors of R, G, and B are received, and these image data are processed. In color image transmission and recording, as defined in the NTSC (National Television System Committee) standards, R, G, and B signals are converted into a luminance signal (Y) and color difference data (e.g., I and Q), and a relatively wide bandwidth is assigned to the luminance signal, thereby obtaining high efficiency The conventional techniques for processing color images as described above are based on color engineering having psychophysics as its background. In any conventional technique, image data of three primary colors, i.e., R, G, and B are utilized.

In order to detect a small difference between colors of objects, it is difficult to accurately discriminate differences between specific colors within a given image in color measurement based on R, G, and B measurement values. When colors have different spectra within a wavelength range of a G color matching function, these colors cannot be clearly discriminated from each other in accordance with G-B color classification.

A multichannel photometer is known as a photometer for measuring a spectrum of light reflected by an object and discriminating colors in accordance with differences in spectra.

This photometer requires expensive units such as a diffraction grating and a high-sensitivity detector array. In addition, when a reflected light spectrum is to be measured, the number of dimensional degrees per unit data is increased, so that an apparatus for processing and analyzing the spectrum data becomes bulky and complicated at high cost, resulting in inconvenience.

The present inventors made extensive studies on optimization of a wavelength range for receiving image data at the time of color information input in accordance with application purposes. The following statistic method is available as a means for determining a wavelength range.

A large number of objects whose correspondences between categories (classes) and spectra of light components reflected by the objects upon irradiation with predetermined illumination light and upon analysis of the reflected light are already known are prepared in units of classes. Spectra of light components reflected by objects in units of classes upon radiation with illumination light are measured. In this manner, a data string of reflected light spectra obtained for each class is called a training set.

The spectrum data of the training set are statistically analyzed such that the intensity of reflected light at each wavelength i plotted along the ordinate and the wavelength is plotted along the abscissa, and that the wavelength range is equidistantly sampled n times to obtain n-dimensional vector data having reflected light intensities of the respective wavelengths as vector elements. The following mathematical technique may be applied as a technique for statistically classifying spectrum patterns prepared as training sets. More specifically, a Foley-Sammon-Trasform (F-S transform) described as a mathematical technique in IEEE Trans. Comp., C-24, 281, (1975) (Reference 1), D. H. Foley and J. W. Sammon Jr., is applied to the above spectrum patterns. That is, the reflected light spectra are classified into two classes in accordance with the F-S transform.

This is a method of obtaining (so as to optimize) vectors suitably classified into two classes in an n-dimensional space having the respective elements of the n-dimensional vector data as orthogonal axes in accordance with an evaluation reference called a Fisher ratio. By using a filter having wavelength characteristics corresponding to classified vectors derived from the F-S transform, the spectra belonging to the two classes and given as training sets can be most efficiently classified.

Another mathematical technique described in Opt. Eng., 23, 728, (1984), Z. H. Gu and S. H. Lee (Reference 2) may be utilized in place of Reference 1. According to the method of Reference 2, optimally classified vectors are obtained for two or more arbitrary classes on the basis of an evaluation reference called a hotelling trace criterion (HTC). Although Reference 2 exemplifies image classification, n-dimensional vector data is used in place of an image expressed as an n-dimensional vector by n pixels, and filter characteristics can be derived in accordance with the above theory.

A method of recognizing and classifying colors is described in a statistic technique for spectrum data in Appl. Opt., 26, 4240 (1987), J. Parkkien and T. Jaaskelainen (Reference 3). According to the method of Reference 3, analysis of major components (K-L transform) of training sets in units of classes is performed, and partial spaces of the respective classes are set. Rotation is performed to eliminate an overlapping portion between the adjacent partial spaces of the classes.

As described above, a method of classifying spectrum patterns to aim at color discrimination can be realized by applying conventional statistic pattern classification methods.

Although filter characteristics derived from any of the conventional statistic techniques are suitable for color classification, they cannot detect a color of a target object recognized with three primary colors, i.e., R, G, and B.

In order to solve this problem, as described in Reference 3, when the method of estimating an original n-dimensional vector (spectrum) from a vector projected into each class partial space is used, estimated spectra can be transformed into R, G, and B values.

In the method described in Reference 3, major component analysis must be repeated until filter characteristics are determined. That is, a covariance matrix is obtained to solve an eigenvalue problem. This operation must be repeatedly performed, and a large amount of arithmetic operations are required. Since the partial spaces are defined in units of classes, a projection operation for determining a correspondence between each vector and each specific class must be repeated in units of classes. That is, an operation for measuring a light intensity through a spectral filter must be repeated in units of classes, thus resulting in a long processing period of time.

SUMMARY OF THE INVENTION

It is the first object of the present invention to provide a color discrimination data input apparatus capable of classifying specific colors belonging to a range of wavelengths which make it difficult to classify, and capable of estimating an original color of a target object by a simple arithmetic operation without using complicated arithmetic processing.

It is the second object of the present invention to provide a color discrimination data input apparatus capable of inputting, as an image, color classification data for classifying specific colors belonging to a range of wavelengths which are difficult to be classified by R, G, and B filters, capable of encoding the color classification data into an image of three primary colors, i.e., R, G, and B by very simple data processing, and capable of facilitating compatibility with imaging equipment.

It is the third object of the present invention to provide a color discrimination data input apparatus capable of classifying specific colors belonging to a range of wavelengths which are difficult to be classified by R, G, and B filters and capable of measuring original colors of target objects.

In order to achieve the first object of the present invention, there is provided a color discrimination data input apparatus comprising image pickup means for converting light reflected by a target object into an electrical signal, a color classification filter having a light-transmitting characteristic suitable for classification of the reflected light, the light transmitting characteristic being designed from a training set by a statistic calculation, means for calculating an absolute color estimation matrix for estimating an original color of the target object, and means for calculating the original color of the target object from the electrical signal of a reflected light intensity obtained through the color classification filter, in accordance with the absolute color estimation matrix.

In order to achieve the second object of the present invention, there is provided a color discrimination data input apparatus comprising image pickup means for converting light reflected by a target object into an electrical signal, a color classification filter having a light-transmitting characteristic suitable for classification of the reflected light, the light transmitting characteristic being designed from a training set by a statistic calculation, a color filter having a light-transmitting characteristic suitable for input of tricolor image, filter control means for switching between the color classification filter and the color filter as needed, and means for encoding an image signal of an object image obtained through the color classification filter into three primary colors on the basis of the light-transmitting characteristic of the color classification filter, and for forming an image upon visualization of the color classification data.

In order to achieve the third object of the present invention, there is provided a color discrimination data input apparatus comprising image pickup means for converting light reflected by a target object into an electrical signal, a color classification filter having a light-transmitting characteristic suitable for classification of the reflected light, the light transmitting characteristic being designed from a training set by a statistic technique, and a color filter having a light-transmitting characteristic suitable for input of tricolor image, and filter control means for switching between the color classification filter and the color filter as needed.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 9A is a view showing a filter having a spectral characteristic of a classification vector $\phi$;

FIG. 9B is a view sowing a filter having a positive spectral characteristic of a classification vector $d_1$;

FIG. 9C is a view sowing a filter having a negative spectral characteristic of a classification vector $d_1$;

FIG. 9D is a view sowing a filter having a positive spectral characteristic of a classification vector $d_2$;

FIG. 9E is a view sowing a filter having a negative spectral characteristic of a classification vector $d_2$;

FIG. 10 is a graph showing classification results of measurement data;

FIG. 18 is a view showing an arrangement of a TV camera and an image processor according to the fifth embodiment of the present invention;

FIG. 19 is a view showing an image input/output apparatus according to the sixth embodiment of the present invention;

DETAILED DESCRIPTION OF THE PREFERRED EMBODIMENTS

The first embodiment to be described below exemplifies a color discrimination data input apparatus of the present invention as a color discrimination apparatus.

Figure 1:
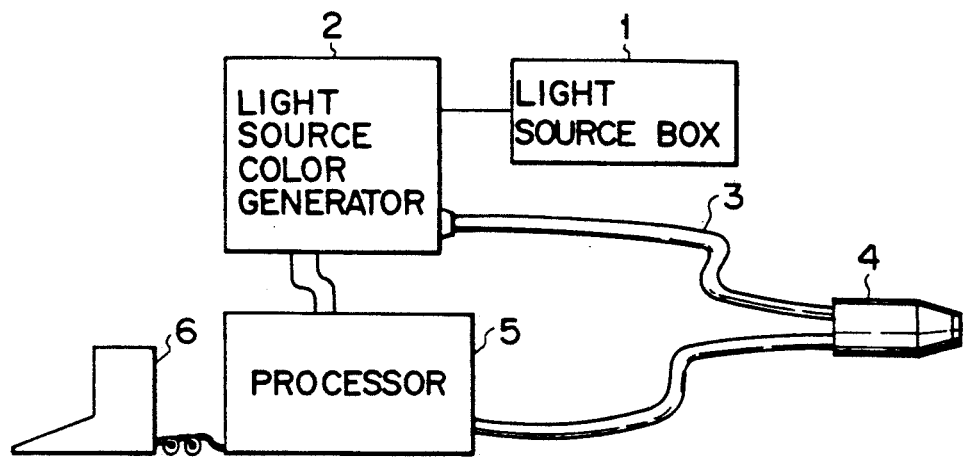
FIG. 1 is a block diagram of a color discrimination apparatus according to the first embodiment of the present invention.

FIG. 1 is a functional block diagram of the first embodiment. This color discrimination apparatus comprises a light source box 1 for generating monochromatic light, a light source color generator 2 for converting the monochromatic light from the light source box 1 into illumination light having a predetermined light intensity (spectrum) and outputting this illumination light, a light guide 3 for guiding the illumination light from the light source color generator 2 to a predetermined position, a detector head 4 for illuminating an object with the illumination light, converting light reflected by the object into an electrical signal, and outputting the electrical signal, a processor 5 for receiving the electrical signal detected by the detector head 4 and performing various types of color discrimination operations, and a man-machine interface (I/F) 6 for inputting an operator's command to the processor 5.

Figure 2:
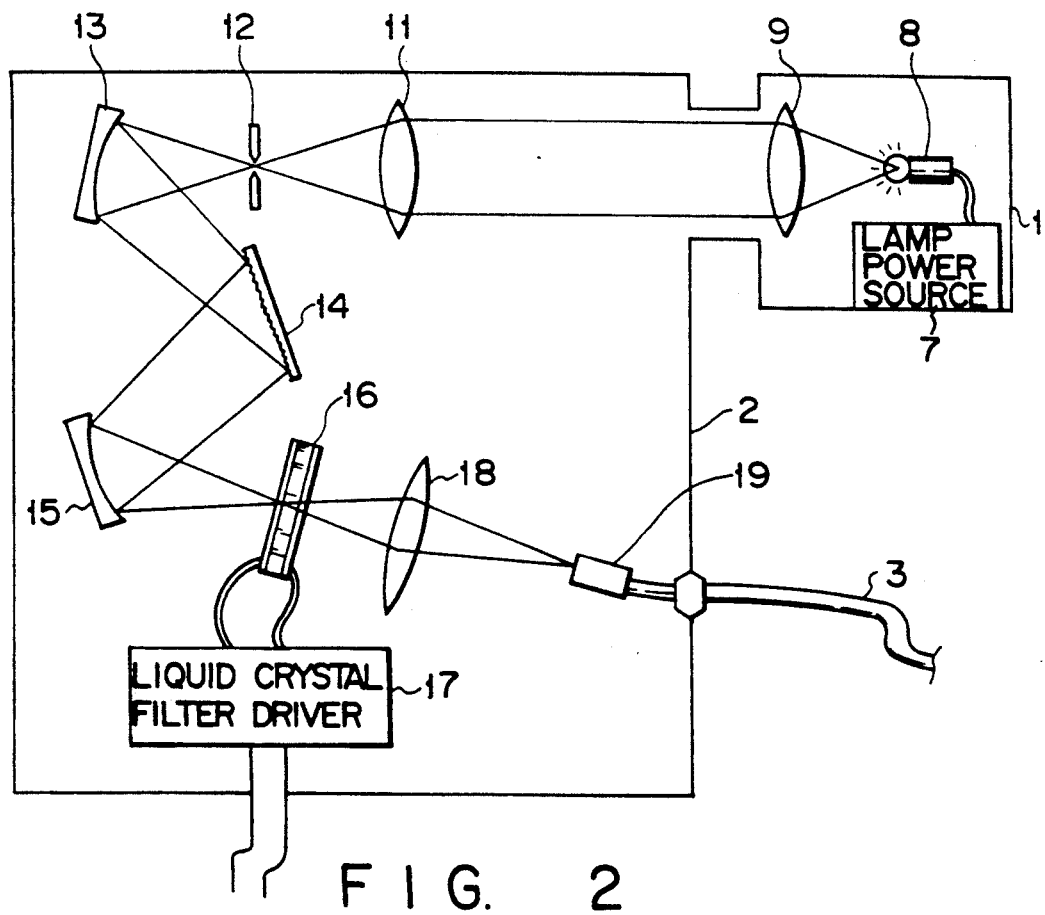
FIG. 2 is a view showing an arrangement of a light source box and a light source color generator in the color discrimination apparatus.

FIG. 2 shows an arrangement of the light source box 1 and the light source color generator 2.

The light source box 1 incorporates a lamp light source 7, and a white light lamp 8 for receiving power from the power source 7. White light emitted by the white light lamp 8 is collimated by a lens 9, and the collimated beam is guided to the light source color generator 2.

A lens 11 for receiving light from a light source side is arranged inside the light source color generator 2. A slit 12 is located at a focal position of the lens 11. A concave mirror 13, a diffraction grating 14, and a concave mirror 15 are arranged in the same manner as in a known spectroscope. A liquid crystal filter 16 is located at the focal plane of the concave mirror 15, i.e., at a position where an output slit is located in a conventional beam splitter. The transmittance of the liquid crystal filter 16 is set to be a desired value by a liquid crystal filter driver 17 controlled by the processor 5. The transmittance can be set to correspond to an image-formation position of each wavelength. The liquid crystal filter 16 constitutes a color classification filter (to be described later). Light having a predetermined wavelength, which is a 1st-order diffracted light from the diffraction grating 14 is attenuated by the liquid crystal filter 1 and is converted into illumination light having a desired spectrum. This illumination light is guided into the light guide 3 and is focused on an end face of an incident-end connector 19 of a bundle of optical fibers.

Figure 3:
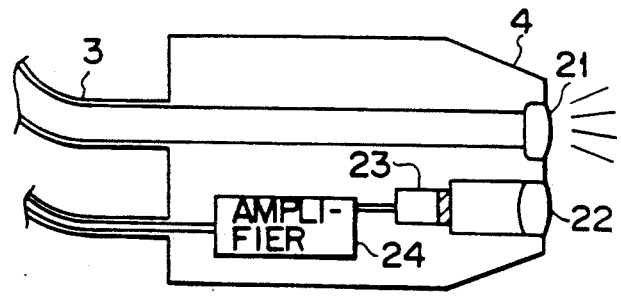
FIG. 3 is a view showing an arrangement of a detector head in the color discrimination apparatus.

The detector head 4 is arranged, as shown in FIG. 3. The illumination light guided through the light guide 3 is radiated on a target object through an illumination lens 21 located at the distal end portion of the detector head 4. Light reflected by the object is focused on the light-receiving surface of a photodetector 23 by means of an objective lens 22 located in the detector head 4. An output signal from the photodetector 23 is supplied to the processor 5 through an amplifier 24.

Figure 4:
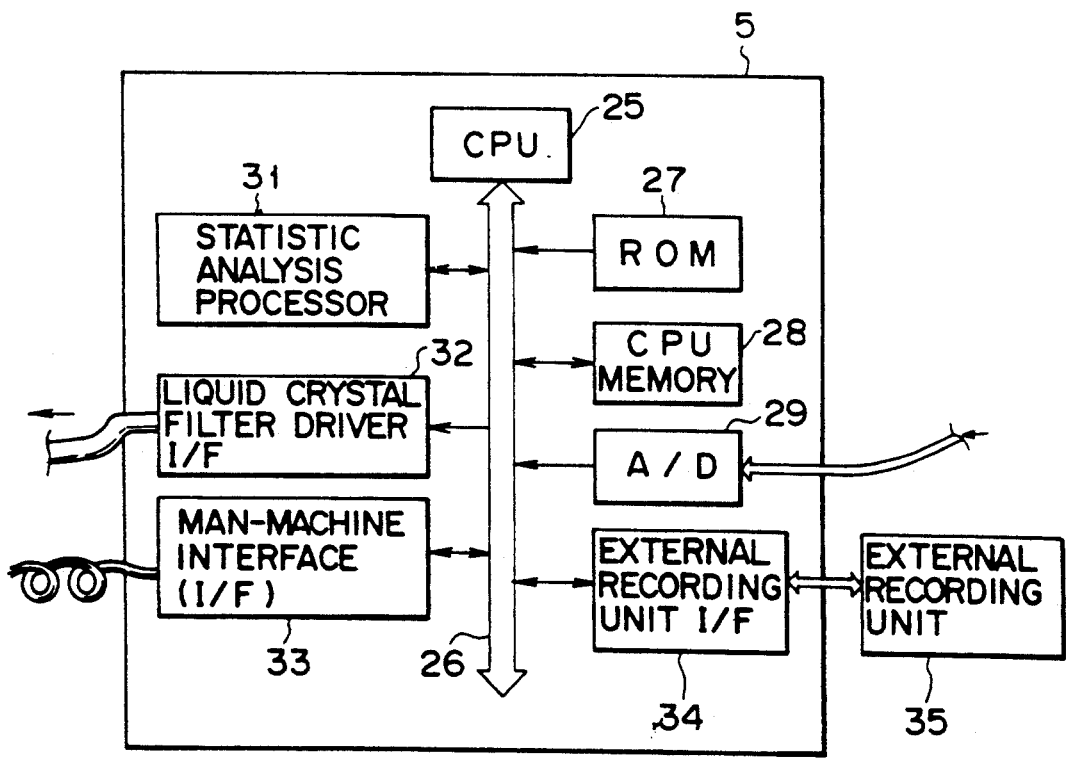
FIG. 4 is a view showing an internal arrangement of a processor in the color discrimination apparatus.

FIG. 4 is a view showing an internal arrangement of the processor 5. A CPU 25 in the processor 5 is connected through an internal bus 26 to a ROM 27, a CPU memory 28, an A/D converter 29, a statistic analysis processor 31, a liquid crystal filter driver interface 32, a man-machine interface 33, and an external recording unit interface 34.

The CPU 25 performs control of the constituting components and hence the apparatus as a whole. The ROM 27 stores an operating system and execution programs under the control of the operating system. An execution program is read out as needed and is then executed. The CPU memory 28 comprises a RAM and stores programs and data at the time of processing execution. The A/D converter 29 inputs a digital output signal from the detector head 4. The statistic analysis processor 31 includes a summation unit, and a memory and can perform a matrix operation at high speed. This processor 31 serves as a special-purpose processor for performing statistic analysis in data generation (to be described later). The liquid crystal filter driver interface 32 is an interface for sending an address and a transmittance determination command signal to the filter driver 17. The man-machine interface 33 is an interface for interfacing a signal input from a keyboard in an operation for outputting a program menu or a measurement result on a display unit. The external recording unit interface 34 is an interface for an external recording unit 35, i.e., a hard or floppy disk driver used for recording a program or a measurement result in a recording medium such as a hard or floppy disk and reading a program or data from the recording medium.

Figure 5:
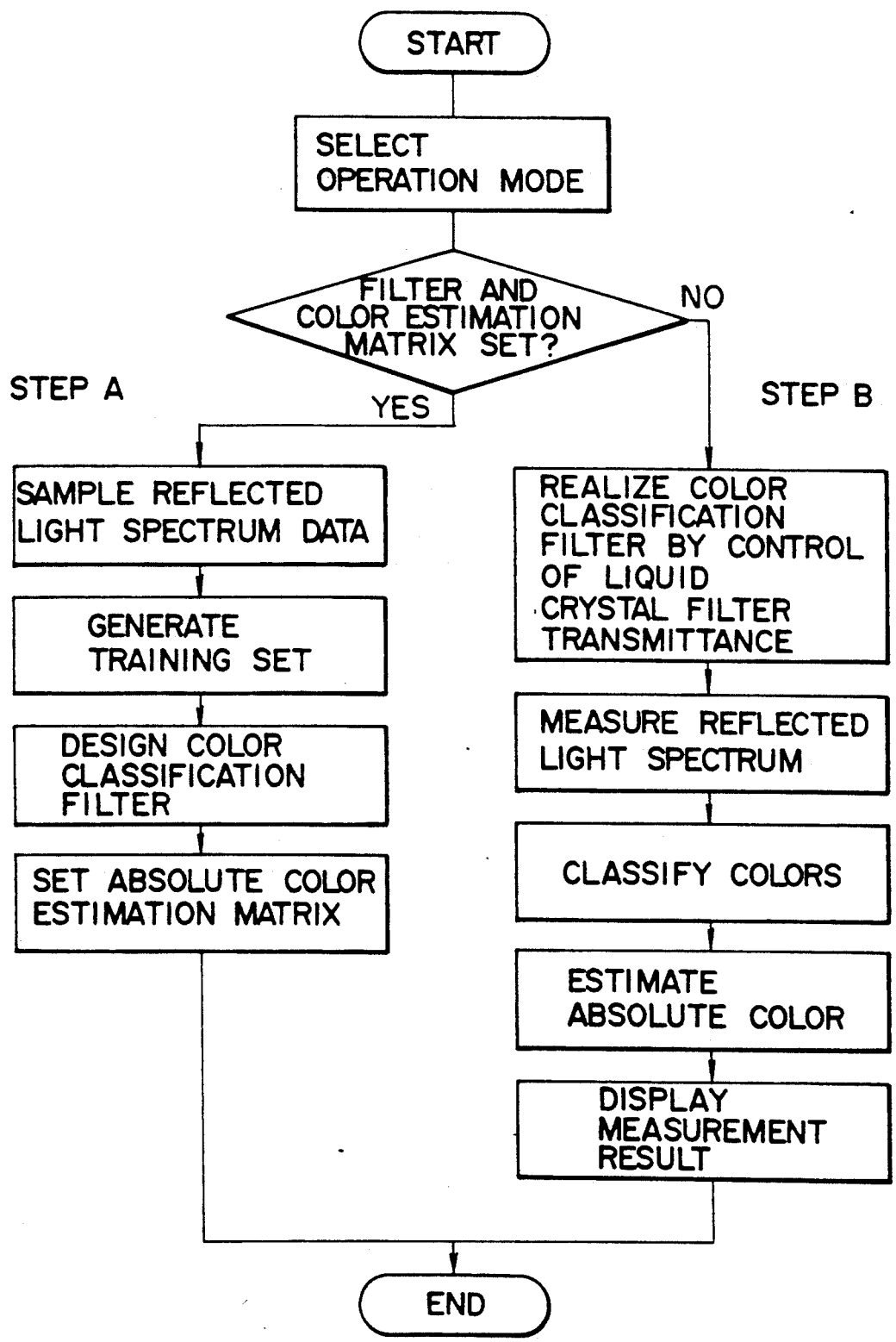
FIG. 5 is a flow chart showing an operation of the processor shown in FIG. 4.

The processor 5 is operated on the basis of a flow chart shown in FIG. 5. The flow chart includes step A for generation a training set to design of a color classification filter and setup of an absolute color estimation matrix, and step B of classifying object colors from actually measured reflected light spectrum data and estimating the absolute colors.

In the first embodiment having the above arrangement, when a color classification filter and an absolute color estimation matrix of a target object are not prepared in advance, step A is executed. The processing contents of step A will be described in detail below.

A plurality of samples having previously known relationships with classes are prepared in units of classes.

Figure 6:
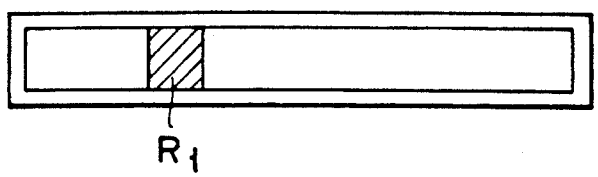
FIG. 6 is a view for explaining an operation for generating a training set.

As shown in FIG. 6, a transmittance distribution of the liquid crystal filter 16 is set so that a region R1 of a specific wavelength becomes maximum. The object is irradiated with illumination light close to monochromatic light from the light source color generator 2 having the liquid crystal filter 16 having the above arrangement. An intensity of light reflected by the object irradiated with this illumination light is measured, and the measured intensity data is stored in the CPU memory 28 in the processor 5.

Figure 7:
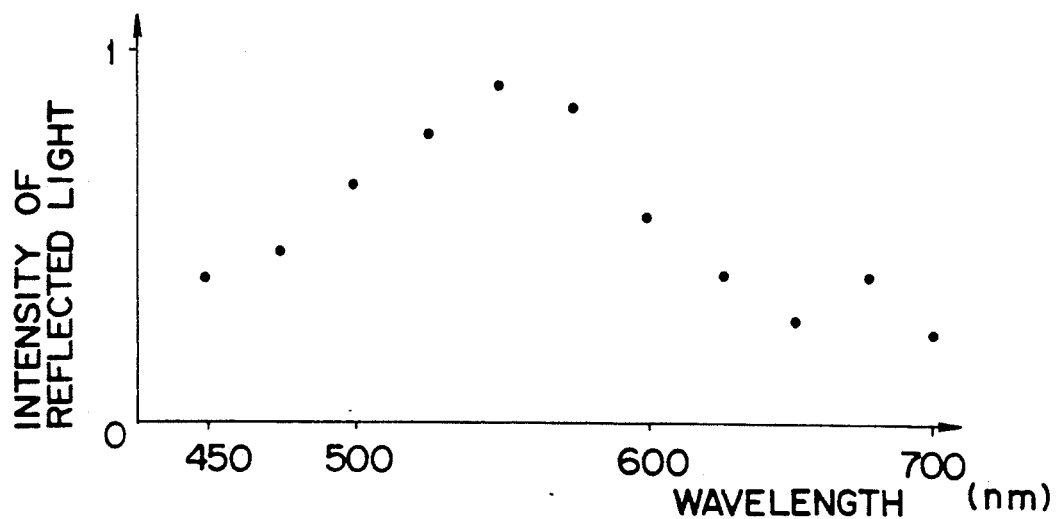
FIG. 7 is a graph of intensities of reflected light components sampled to generate a training set.

The above wavelength region R1 is shifted, and the above operations are repeated. Intensities of light components having wavelength regions obtained by dividing a total wavelength range into n (n is several tens of an integer) regions are recorded. The measured spectrum data are shown in FIG. 7. In the data string shown in FIG. 7, spectrum data are obtained by measuring intensities of reflected light components in a total of 11 wavelength regions at 25-nm intervals in the total wavelength range of 450 nm to 700 nm.

Spectrum data of the respective classes for all the samples prepared in advance are measured to obtain a training set. When a total volume of data is increased, data may be temporarily stored in a hard or floppy disk by the external recording unit 35.

A technique for designing a color classification filter having a spectral characteristic suitable for classifying the data from the prepared training set will be described below. Assume that the number of classes is defined as k, and the number of data in the training set of each class is defined as mi (i=1, . . . k).

The first design technique will be described below. In this case, the number of classes is set to be k=2. Two classes are called classes 1 and 2. Reference colors belong to class 1, while colors with tints different from those of the colors of class 1 belong to class 2. The training sets of classes 1 and 2 are defined as follows:

Class 1: $\{x_1^{(1)}, x_2^{(1)}, \ldots x_{m1}^{(1)}\}$

Class 2: $\{x_1^{(2)}, x_2^{(2)}, \ldots x_{m2}^{(2)}\}$ (1)

In this case, each data is represented by an n-dimensional vector as follows:

$$x_q(p) = [x_1^{pq}, x_2^{pq}, \ldots x_n^{pg}] \quad p = 1,2 \quad q = 1,2,\ldots mp \quad (2)$$

Major component analysis (K-L transform) of the training set of class 1 is performed. That is, the following intraclass covariance matrix $S_2^{(1)}$ is calculated from the training set of class 1 to solve an eigenvalue problem:

$$S_2^{(1)} = \sum_{j=1}^{m1} (x_j^{(1)} - \overline{x}^{(1)})(x_j^{(1)} - \overline{x}^{(1)})^t \quad (3)$$

where, $X^{(1)}$ is an average vector of class 1.

$$\overline{x}^{(1)} = \sum_{j=1}^{m1} P(x_j^{(1)}) \cdot x_j^{(1)} \quad (4)$$

where $P(X_j^{(1)})$ is a generation probability of data $X_j(1)$ of the training set.

A characteristic equation of $S_2^{(1)}$ can be written as follows:

$$S_2^{(1)} \phi = \lambda_i \phi_i \quad (i=1, 2, \ldots n) \quad (5)$$

where $\phi_i$ is an eigenvector, and $\lambda_i$ is an eigenvalue. Assume that a range of $S_2^{(1)}$ is given as r (r<n), and that an orthogonal complementary space U of the first major component vector $\phi_i$ is taken into consideration within a space constituted by r eigenvectors $\phi_i$ (i=1, 2, . . . r):

$$U = \{\phi_2, \phi_3, \ldots \phi_r\} \quad (6)$$

The data of the training sets of classes 1 and 2 are projected or mapped into the space U by equation (7) to reduce the dimensional degree of the training set, and the projected result serves as a new training set as follows:

$$y_\phi^{(p)} = Ru x_q^{(p)} \quad (7)$$

for $$Ru = [\phi_2, \phi_3, \phi_r]^t \quad (8)$$

The new training set can be represented as follows:

Class 1: $\{y_1^{(1)}, y_2^{(2)}, \ldots y_{m1}^{(1)}\}$

Class 2: $\{y_1^{(2)}, y_2^{(2)}, \ldots y_{m2}^{(2)}\}$ (9)

The data $y_q^{(p)}$ is the (r−1)-dimensional data.

A vector $d_1u$ for maximizing a Fisher ratio represented by equation (10) is obtained in the new training set represented by equation (9):

$$F(d^u) = \frac{(d^u)^t \cdot S_1^u \cdot d^u}{(d^u)^t \cdot S_2^u \cdot d^u} \quad (10)$$

where $S_1^u$ is calculated by an interclass covariance matrix by equation (11):

$$S_1^u = \sum_{i=1}^{2} pi(y^{(i)} - y^o)(y^{(i)} - y^o)^t \quad (11)$$

Pi is defined as a generation probability of the ith class, and $\overline{y}^{(i)}$ is defined as an average vector of the ith class, so that the following equation is derived:

$$\overline{y}^{(i)} = \sum_{j=1}^{mi} P(y_j^{(i)}) \cdot y_j^{(i)} \quad (12)$$

An average vector $\overline{y}^o$ of all the training sets is given as follows:

$$\overline{y}^o = \sum_{i=1}^{2} pi \cdot y^{(i)} \quad (13)$$

$S_2^u$ is an average value of the intraclass covariance matrix and is represented as follows:

$$S_2^u = \sum_{i=1}^{2} p_i S_2^{u(i)} \qquad (14)$$

In this case, an intraclass covariance matrix $S_2^{u(i)}$ can be similarly defined as in equation (3):

$$S_2^{u(i)} = \sum_{j=1}^{m_i} (y_j^{(i)} - \bar{y}^{(i)})(y_j^{(i)} - \bar{y}^{(i)})^t \qquad (15)$$

The vector $d_1^u$ is finally derived as follows:

$$d_1^u = \partial_1 (S_2^u)^{-1} \Delta^u \qquad (16)$$

for $$\Delta^u = \bar{y}^{(1)} - \bar{y}^{(2)} \qquad (17)$$

where $\partial_2$ is the normalization constant to define $(d_1^u)^t \cdot d_1^u = 1$.

When a vector $d_2^u$ for maximizing the Fisher ratio in a space perpendicular to the vector $d_1^u$ in the space U is obtained, the vector $d_2^u$ represented by the following equation can be derived:

$$d_2^u = \partial_2 (S_2^u)^{-1} \left[ I - \frac{(\Delta^u)^t [(S_2^u)^{-1}]^3 \Delta^u}{(\Delta^u)^t [(S_2^u)^{-1}]^2 \Delta^u} \cdot (S_2^u)^{-1} \right] \Delta^t \qquad (18)$$

where $\partial_2$ is the normalization constant to define $(d_2^u)^t \cdot d_2^u = 1$.

The Fisher ratio is an evaluation reference representing a degree of separation between classes when data is projected on the vector $d^u$. The vectors $d_1^u$ and $d_2^u$ are the first two orthogonal vectors for maximizing the Fisher ratio in the space U. Theoretically, although $(r-1)$ number of orthogonal vectors can be calculated from a larger one, only two orthogonal vectors are enough for two classes. Since the vectors $d_1^u$ and $d_2^u$ are $(r-1)$-dimensional vectors, these vectors can be transformed into n-dimensional vectors $d_1$ and $d_2$:

$$d_i = Ru^t d_i^u \qquad (19)$$

A filter for realizing spectral characteristics of three vectors is set as follows:

$$Q = \{\phi_1, d_1, d_2\} \qquad (20)$$

The vector $\phi_1$ in the above equation represents an average vector of data of class 1. This filter serves as a filter for measuring an intensity of totally reflected light. The vectors $d_1$ and $d_2$ represent light-transmitting characteristics for most efficiently classifying the spectral components of light reflected by the objects into classes 1 and 2.

When the filter having spectral characteristics represented by the above vectors $d_1$ and $d_2$ is designed, a transmittance distribution of the liquid crystal filter 16 for realizing this filter by means of the liquid crystal filter 16 must be determined. Transmittance distribution data is stored in a memory in the processor.

Another filter design technique will be described below. In the above statistic technique has two classes. However, in this method, the number of classes is k.

As in the first method, training set data are projected onto an orthogonal complementary space U (i.e, the space U is an $(r-1)$-dimensional space, where r is the rank of a covariance matrix $S_2^{(1)}$ of class 1) of the first major component vector of a reference class (defined as class 1), and new training sets are prepared as follows:

Class 1: $\{x_1^{(1)}, x_2^{(1)}, \ldots x_m^{(1)}\}$

Class 2: $\{x_1^{(2)}, x_2^{(2)}, \ldots x_m^{(2)}\}$

Class k: $\{x_2^{(k)}, x_2^{(k)}, \ldots x_m^{(k)}\} \qquad (21)$

A matrix H for maximizing hotelling trace criterion (to be referred to as an HTC hereinafter) represented as follows is obtained:

$$J = tr[(S_2^u)^{-1} S_1^u] \qquad (22)$$

where "tr" is the operator for extracting oblique components of the matrix and operating them, and HTC is an evaluation reference representing a degree of separation between classes. The matrix H can be derived by the following procedures. First, an eigenvalue problem of the average $S_2^u$ of the intraclass covariance matrix is solved as follows:

$$S_2^u T' = T' \Lambda' \qquad (23)$$

The average $S_2^u$ is transformed by a transform matrix $\Lambda T^{-\frac{1}{2}}$ for whitening the average $S_2^u$ to obtain a matrix D as follows:

$$D = (\Lambda^{-\frac{1}{2}} T) S_1^u (\Lambda^{-\frac{1}{2}} T)^t \qquad (24)$$

where $\Lambda$ is a full-rank partial matrix of $\Lambda'$ in equation (23):

$$\Lambda' = \begin{bmatrix} \Lambda & 0 \\ 0 & 0 \end{bmatrix} \qquad (25)$$

and T is a matrix except for an eigenvector corresponding to an eigenvalue of "0" from T' in equation (23).

A D eigenvalue problem will be solved:

$$D \psi = \psi T \qquad (26)$$

The transform matrix H is constituted by the following equation:

$$H = \psi \Lambda^{-\frac{1}{2}} U^t \qquad (27)$$

The average $S_2^u$ in equation (23) and $S_2^u$ in equation (24) are obtained as in equations (14) and (11).

The matrix H represented by equation (27) includes the number $(k-1)$ of effective row vectors $(i = 1, 2, \ldots k-1)$:

$$H = \begin{bmatrix} (d_1^u)^t \\ (d_2^u)^t \\ \cdot \\ \cdot \\ \cdot \\ (d_{k-1}^u)^t \end{bmatrix} \qquad (28)$$

This vector is transformed into an n-dimensional vector $d_i$ as in equation (19) as follows:

$$d_i = Ru^t \cdot d_i^u \qquad (29)$$

Finally, a filter for realizing spectral characteristics of the next the number k vectors is finally set:

$$Q = [\phi_1, d_1, d_2, \ldots d_{k-1}] \quad (30)$$

where $\phi_1$ is the average vector of data of class 1 and serves as a filter for measuring an intensity of totally reflected light, and $d_i$ represents spectral characteristics for obtaining k classes.

According to either method described above, effective vectors for classification are derived from an orthogonal complementary space of the first major component vector in the space constituted by effective eigenvectors of class 1. The space defined by equations (20) and (30) is close to the major component space of class 1 and is effective for reconstruction of the n-dimensional original vector. In addition, since classification vector calculations are performed after the n-dimensional vector is transformed into the $(r-1)$-dimensional vector, a total calculation amount can be greatly reduced. Therefore, the above technique is suitable for effective vector classification and estimation of an original spectrum, and the total operation amount is small, resulting in a practical application.

In step A after the color separation filter is designed, an absolute color estimation matrix is set. The absolute color estimation matrix is used as a matrix for transforming the color classification data obtained by the color classification filter into data of three primary colors, i.e., R, G, and B.

This calculation method will be described below. The first method is to estimate a spectrum itself. A transform matrix constituted by a set of spectral characteristics obtained by equations (20) and (30) is defined as A:

$$A = [\phi, d_1, \ldots d_{l-1}] \quad (31)$$

When a spectrum vector x is transformed by A to measure data V, this data is given as follows:

$$V = Ax \quad (32)$$

Hence, the data V has the same dimensional degree 1 as the number of spectral filters. Since $1 < n$ is established, no inverse matrix is present in the matrix A. For this reason, although the spectrum vector x cannot be perfectly obtained from the data, the spectrum vector x can be estimated from a pseudo inverse matrix $A^+$ as follows:

$$A = A'(AA')^{-1} \quad (33)$$

In particular, when the set of spectral filters obtained by equation (20) are used, the matrix A becomes an orthogonal matrix, so that the pseudo inverse matrix $A^+$ can be given as follows:

$$A^+ = A' \quad (34)$$

In addition to simple calculations, since the matrix A is constituted by a transform matrix for performing transformation of the vectors into an orthogonal space very close to the space constituted by the major component vectors of the training set, an excellent approximation result can be obtained. When a set of spectral characteristics obtained by equation (30) are used, since the matrix A is the transform matrix for performing transformation to a space close to the major component space of the training set and the dimensional degree l of the measurement data $v$ is large, good approximation estimation can be performed with a good pseudo inverse matrix $A^+$ of equation (33). The spectrum $\tilde{x}$ estimated by the pseudo inverse matrix $A^+$ is defined as follows:

$$\tilde{x} = A^+ v \quad (35)$$

R, G, and B values can be derived from the above estimation spectrum. For example, if a matrix for deriving the R, G, and B values from the above spectrum is defined as C, a 3-dimensional vector having R, G, and B values as its components is given as follows:

$$r = cx_1 \quad (36)$$

for $c = [C_r, C_g, C_b]'$ where $C_r$, $C_g$, and $C_b$ are color matching functions of the R, G, and B colors, respectively.

The R, G, and B values r estimated by the measurement data v using the matrix v can be given as follows:

$$r = CA^+ v \quad (37)$$

Therefore, a matrix B for estimating the R, G, and B values can be set as follows:

$$B = CA^+ \quad (38)$$

The transform matrix B thus set is stored in the memory in the processor.

A Wiener estimation method for suppressing additive noise mixed in the measurement data v will be described as a second method. The measurement data v is represented by the following equation in place of equation (32):

$$v = Ax + n \quad (39)$$

where n is the vector representing noise.

An estimation spectrum $\tilde{x}$ is calculated by the following equation:

$$x = Wv \quad (40)$$

When a matrix W for minimizing a square error of the estimation spectrum $\tilde{x}$ and an original spectrum $x$ is obtained, the following equation is derived:

$$W = KxA'(AKxA' + Kn)^{-1} \quad (41)$$

where Kx is the covariance matrix of the original spectrum, and Kn is the noise covariance matrix. The covariance matrix $S_2(1)$ of class 1 is substituted into equation (3). In addition, if noise represented by equation (39) is assumed to be white noise, the following condition can be given:

$$Kn = \sigma^2 n II \quad (42)$$

where $\sigma^2 n$ is noise dispersion, so that the noise dispersion value is estimated from characteristics of a measuring system in advance, and a matrix W of equation (41) is set. Finally, a matrix B for estimating the R, G, and B values from the measurement data can be calculated as follows in the same manner as in equation (38):

$$B = CW \quad (43)$$

A method of deriving B in the following equation by a method of least squares for directly estimating the R, G, and B values $\bar{r}$ from the measurement data will be described as the third method:

$$\bar{r} = Bv \quad (44)$$

An average square error between the R, G, and B values obtained from the original spectrum by equation (32) and the R, G, and B values estimated by equation (44) is defined as follows:

$$\epsilon = tr[E\{ r - \bar{r} ( r - \bar{r} )^t \}] \quad (45)$$

where $E\{r-\bar{r}(r-\bar{r})^t\}$ is the operator representing averaging. In order to obtain B for minimizing $\epsilon$, the following differential equation is established:

$$\frac{\partial}{\partial B^t} \epsilon = 0 \quad (46)$$

A solution of equation (46) yields the following equation:

$$B = K vr K v^{-1} \quad (47)$$

where Kvr is the mutual covariance matrix between v and r, and Kv is a covariance matrix of v and, these matrices can be represented by the following equations:

$$Kvr = E\{ ( v - \bar{v} )( r - \bar{v} ) \} \quad (48)$$

$$Kv = E\{ ( v - \bar{v} )( v - \bar{v} ) \} \quad (49)$$

Equations (48) and (49) are statistically obtained in preprocessing. More specifically, Kvr and Kv are obtained by using v calculated by the transform matrix A obtained by the above method and the R, G, and B values r obtained by equation (36). More specifically, the following calculations are performed by the processor 5 in practice:

$$Kvr = \sum_{j=1}^{ml} (v_j^{(1)} - \bar{v}_j^{(1)})(r_j^{(1)} \cdot \bar{r}_j^{(1)})^t \quad (50)$$

$$Kv = \sum_{j=1}^{ml} (v_j^{(1)} - \bar{v}_j^{(1)})(r_j^{(1)} \cdot \bar{r}_j^{(1)})^t \quad (51)$$

In equations (50) and (51), a training set of class 1 is calculated. However, training sets of a plurality of classes or all the classes may be calculated.

When color measurement of an object is to be performed, the microprocessor performs processing of step B. The processing contents of step B will be described in detail below.

Figure 8:
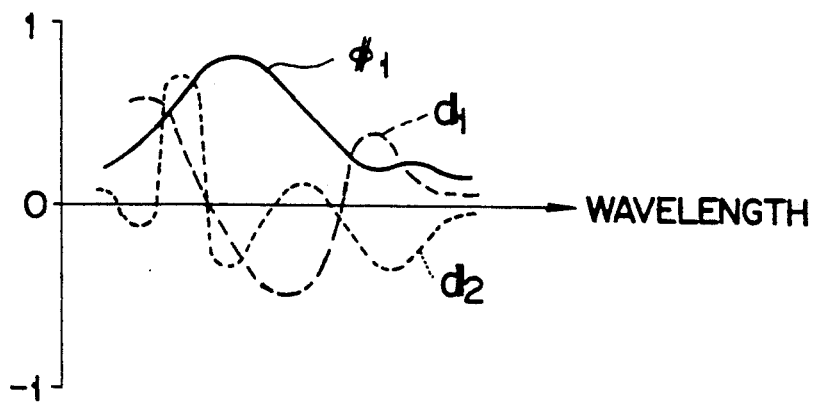
FIG. 8 is a graph showing spectral characteristics of color classification vectors.

FIG. 8 shows a spectral characteristic of a color classification filter obtained in step A. In practice, each spectral characteristic is obtained in the form of an n-dimensional vector. However, for illustrative convenience, the spectral characteristics are represented by a continuous line in FIG. 8. Since the vectors are perpendicular or almost perpendicular to each other, vectors $d_1$ and $d_2, \ldots$ from the second vectors have positive and negative characteristics. In order to realize these spectral characteristics by the liquid crystal filter 16, two filters, i.e., positive and negative region filters for each arbitrary vector spectral characteristic, must be prepared. A set of spectral characteristics obtained in step A is defined as $Q = \{\phi_1, d_1, \ldots dl_{-1}\}$, a set of spectral filters set in the liquid crystal filter 16 in practice is given as $Q' = \{\phi_1, d_1^+, d_1^-, \ldots d_{l-1}^+, d_{l-1}^-\}$ wherein the vector $d_1^+$ is a positive component of the vector $d_1$ and the vector $d_1^-$ is its negative component.

Actual filters realized by controlling the transmittance distribution of the liquid crystal filter 16 are shown in FIGS. 9A to 9E. Light components reflected by objects are obtain by the five color classification filters shown in FIGS. 9A to 9E, respectively. A transform value Vi (i=1, ... i−1) by the vector $d_1$ is obtained as follows:

$$V_i = d_i x = d_i^+ x - d_i^- x \quad (52)$$

and classification is performed by using the above value.

As shown in FIG. 10, a threshold value ti of each classification vector $d_i$ (i=1,...1−1) is determined and is compared with the measurement value vi to perform classification. A determination reference may be given by a line in a classification space:

$$\beta_1 \cdot 1 + \ldots + \beta_{l-1} \cdot l_{-1} = \xi \quad (53)$$

In this case, the following transformation is performed:

$$\omega = \beta_1 V_1 + \ldots \beta_{l-1} \cdot d_{l-1} = \xi \quad (54)$$

and $\omega$ and $\xi$ are compared to perform classification.

The classification result thus obtained is displayed on a display unit in the man-machine interface 6. Plotting of data in the classification space shown in FIG. 10 may be performed on the display unit in the man-machine interface 6, so that an observer can judge the display contents.

The original spectrum and the R, G, and B values are estimated for the classified color classification data by using the transform matrices $A^+$, W, and B obtained in step A. This estimation result is displayed on the display unit in the man-machine interface 6.

In this embodiment, at the time of design of the classification filters in step A, since the color classification vectors are calculated after the n-dimensional data is transformed into the (r−1)-dimensional data, the number of operations can be greatly reduced. In addition, since absolute colors can be estimated from the color classification vectors in accordance with relatively easy operations, original spectra can be estimated by a small number of operations as compared with Reference 3 described above.

In addition, there is provided a system for systematically performing operations from design of color classification filters and setup of absolute color estimation matrices to classification and estimation of colors. This system can perform color classification and absolute color recognition within a short period of time.

In order to achieve the third object of the present invention, the following function is achieved by the arrangement of this embodiment. I order to classify specific colors, the liquid crystal filter 16 is set to have a transmittance distribution of the color classification filter to perform highly efficient color classification. In this case, the light-transmitting characteristics of the color classification filters can be obtained by classification vectors obtained by directly applying a statistical classification method without performing arithmetic operations for transforming the n-dimensional data into the (r−1)-dimensional data. In order to measure original colors of the target objects, the liquid crystal filter 16 is set to have a transmittance distribution of the R, G, and B color filters and is operated in the same manner as in the conventional color measuring apparatus.

The second embodiment which exemplifies an electronic endoscope according to the present invention will be described below.

Figure 11:
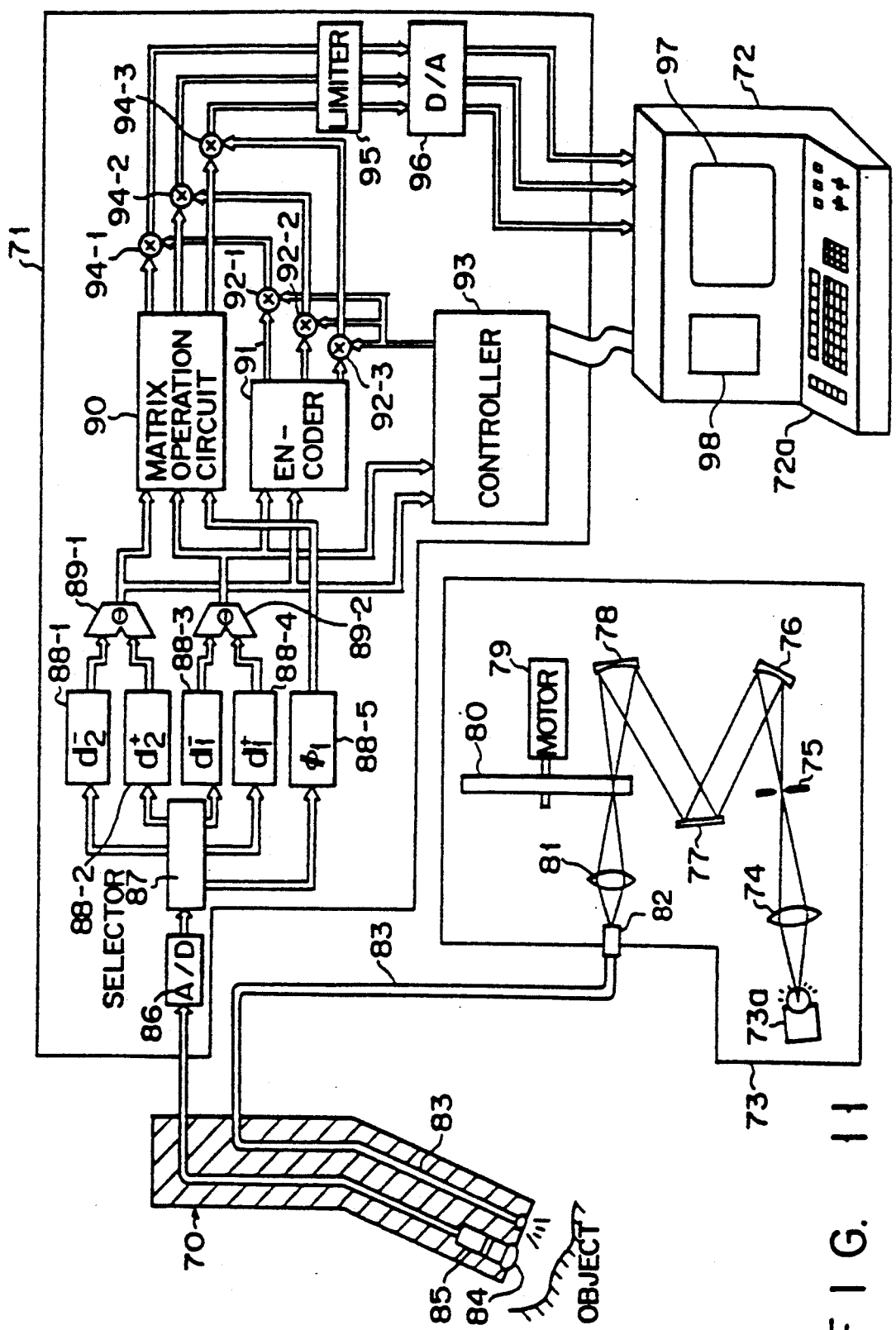
FIG. 11 is a block diagram of a electronic endoscope according to the second embodiment of the present invention.

FIG. 11 is a view showing an arrangement of the electronic endoscope according to the second embodiment.

This electronic endoscope comprises an endoscope 70, a processor 71, a man-machine interface 72, and an illumination system 73 as major components.

In the illumination system 73, illumination light emitted by a white color lamp 73a passes through a lens and a slit 75 located at the focal plane of the lens 74. The illumination light is then collimated by a concave mirror 76, and the collimated light is incident on a diffraction grating 77. The 1st-order light diffracted at a predetermined angle corresponding to a wavelength is focused by a concave mirror 78. A rotary filter 80 is located on the focal plane and is controlled by a motor 79. Light passing through the rotary filter 80 is focused on an incident-end connector by a lens 81.

Figure 13:
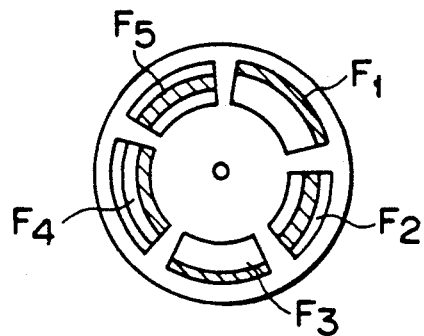
FIG. 13 is a filter shown in FIG. 11.

The rotary filter 80 comprises (2l−1) (where l is the number of color classification filters; in this embodiment l=3) filters aligned in a rotational direction, as shown in FIG. 13. The color classification filters comprise five (i.e., F1 to F5) spectral filters for realizing the light-transmitting characteristics of the color classification vector $d_1$, the vector $d_2$, and the vector $\phi_1$. Since the color separation vector $d_1$ and the vector $d_2$ include positive and negative components, positive and negative filters are prepared for these vectors. The rotary filter 80 is constituted by an ND filter which realizes a transmittance distribution in accordance with a predetermined wavelength characteristic in the radial direction. The motor 79 is controlled to be rotated by one revolution per 30 seconds, and illumination light components are sequentially radiated by the five filters within a one-frame period.

The endoscope 70 is arranged such that the illumination light incident on the incident-end connector 82 is guided to an object through the light guide 83. The object is irradiated with the illumination light exiting from the distal end portion of the light guide 83. More specifically, the object is illuminated by the color classification filters F1 to F5 within each one-frame period. Light reflected by the object irradiated with the illumination light is focused by an objective lens 84 located at the distal end portion of the endoscope 70 and is picked up by an image pickup camera 85.

The processor 71 causes an A/D converter 86 to convert an image signal from the image pickup camera 85 into a digital signal. The output terminal of the A/D converter 86 is connected to frame memories 88-1 to 88-5 through a selector 87. The selector 87 causes the frame memories 88-1 to 88-5 to store corresponding image signals input by the five spectral filters F1 to F5. That is, two images input by the positive and negative filters of the vector $d_2$ are stored in the frame memories 88-1 and 88-2, and two images input by the positive and negative filters of the vector $d_1$ are stored in the frame memories 88-3, and 88-4, respectively. An image input by the filter having the characteristic of the vector $\phi_1$ is stored in the frame memory 88-5.

The image signals stored in the frame memories 88-1 and 88-2 are input to a subtracter 89-1, and the image signals stored in the frame memories 88-3 and 88-4 are input to a subtracter 89-2. The positive and negative components of the vectors $d_1$ and $d_2$ are subtracted from each other to obtain an image derived from the vectors $d_1$ and $d_2$. The resultant image is input to a matrix operation circuit 90. The image stored in the frame memory 88-5 is also input to the matrix operation circuit 90.

The matrix operation circuit 90 is arranged to convert the image of the vectors $\phi_1$, $d_1$ and $d_2$ by the transform matrix B into R, G, and B values. The images of the vectors $d_1$ and $d_2$ output from the subtracters 89-1 and 89-2 are input to an encoder 91. The encoder 91 outputs predetermined coefficients $g_r$, $g_g$, and $g_b$ corresponding to the R, G, and B values in accordance with the magnitudes of the input values. The coefficients $g_r$, $g_g$, and $g_b$ are output to multipliers 92-1 to 92-3, respectively, and are multiplied with a gain $\alpha$. The gain $\alpha$ is set by an observer at an operation unit 72a in the man-machine interface 72 and is output to a controller 93.

The resultant coefficient values $ag_r$, $ag_g$, $ag_b$ are multiplied with the R, G, and B values output from the matrix operation circuit 90 by multipliers 94-1 to 94-3. Products $ag_rR$, $ag_gG$, and $ag_bB$ respectively output from the multipliers 94-1 to 94-3 are input to a limiter 95, so that input components exceeding the threshold value set in the limiter 95 are cut. The processed results ar converted into analog video signals by a D/A converter 96. The image of the vectors $d_1$ and $d_2$ is input to the controller 93 as needed to check whether a value belonging to an abnormal class is present in accordance with magnitudes of values.

On the other hand, the D/A-converted analog video signal is displayed on a TV monitor 97 incorporated in the man-machine interface 72. At the same time, class information output from the controller 93 is displayed on a display 98. The display 98 also displays operation menu and various conditions in a normal display mode.

The magnitudes of values of the classification vectors $d_i$ (i=1, 2, ... l) represent classes, so that pseudo color display is performed by encoding the classification vectors into the R, G, and B values. Therefore, classes can be clearly displayed in different colors.

For example, the above display can be performed as follows. If the l-dimensional data is V, the R, G, and B values estimated by the v-dimensional data are given as $\bar{r}$, and the encoding matrix is defined as G, a pseudo color $r_p$ can be represented as follows:

$$\bar{r}_p = \alpha G \bar{r} = \alpha GBV \tag{55}$$

for $$G = \begin{bmatrix} g_r & & 0 \\ & g_g & \\ 0 & & g_p \end{bmatrix} \tag{56}$$

The $g_r$, $g_g$, and $g_b$ values are obtained by encoding the difference between $V_1$ and $t_1$ into G values when the value $v_1$ obtained by the spectral filter $d_1$ is classified by a given threshold value $t_1$. That is, the $g_r$, $g_g$, and $g_b$ values are obtained as follows:

$$g_r = -(C/2)(V_1 - t_1) + 1$$

$$g_g = C(V_1 - t_1) + 1$$

$$g_b = -(C/2)(V_1 - t_1) + 1 \tag{57}$$

where C is the constant for properly performing transformation of the difference $(V_1-t_1)$.

By setup using equations (57), a color belonging to a given class and having a positive difference $(V_1-t_1)$ becomes more greenish, but a color belonging to this class and having a negative difference $(V_1-t_1)$ becomes less greenish and has a higher tint of magenta defined as a color complementary to green. Therefore, a difference between classes can be emphasized by a pseudo color display.

The endoscope described above has neither a function of designing color classification filters nor a function of setting an absolute color estimation matrix. Data associated with the color classification filters and the absolute color estimation matrix are prepared beforehand by the following apparatus.

Figure 12:
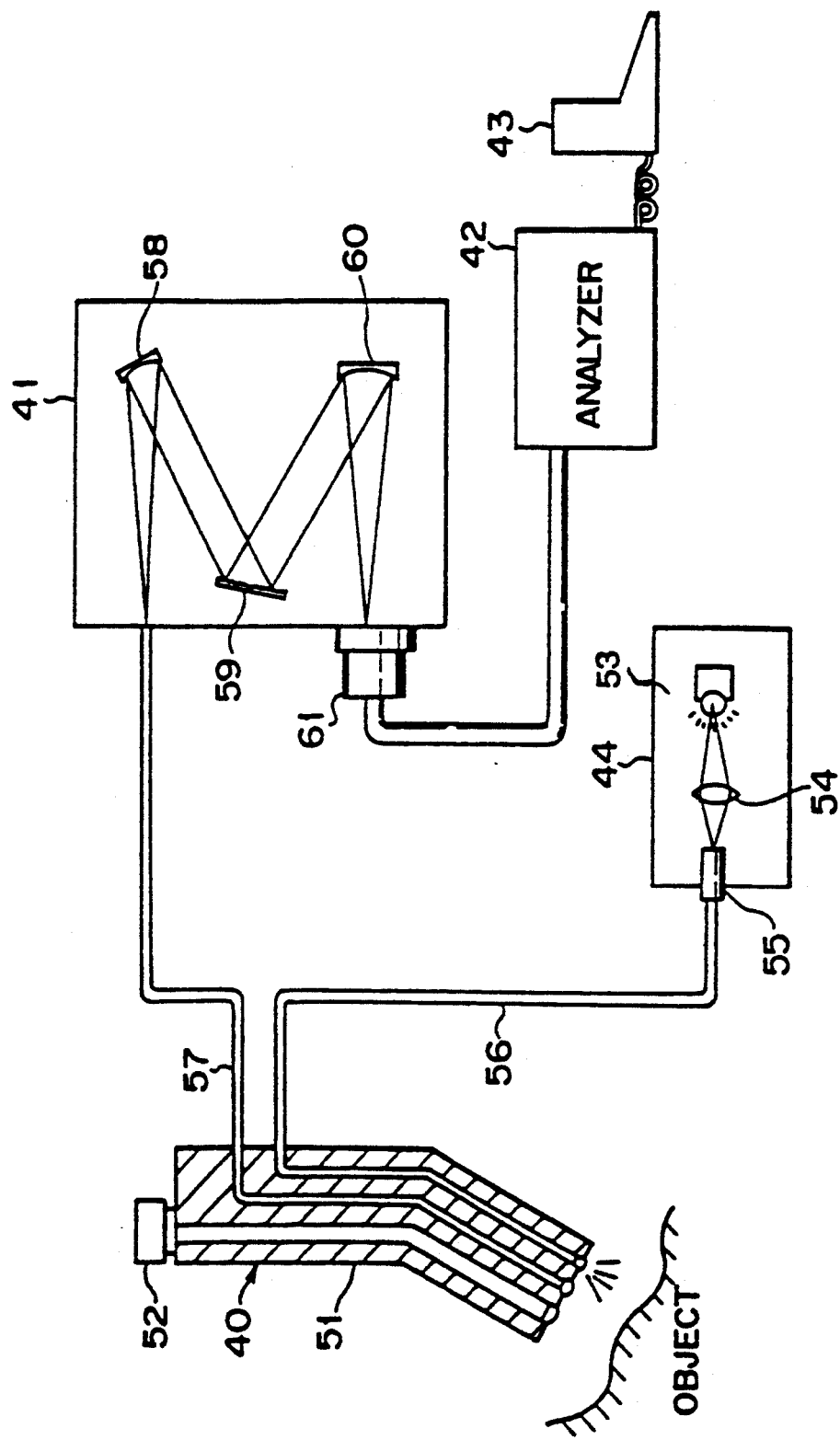
FIG. 12 is a block diagram of a classification filter used in the electronic endoscope shown in FIG. 11 and a data generator for designing an absolute color estimation matrix.

An arrangement of this apparatus is shown in FIG. 12.

This apparatus includes an endoscope 40, a polychromator 41, an analyzer 42, a man-machine interface 43, and a light source 44.

An operator can observe an object from an eyepiece 52 of an image guide 51 in the endoscope 40. Illumination light emitted by a white color lamp 53 in the light source 44 is focused on an incident-end connector 55 by a lens 54 and is then emitted from the distal end portion of the endoscope 40 through a light guide 56. Light reflected by the object is guided to a light guide 57 and is incident on the polychromator 41. The polychromator 41 comprises a concave mirror 58 for collimating light incident on the polychromator 41, a diffraction grating 59 for receiving the collimated light from the concave mirror 58, and a concave mirror 60 for focusing light reflected by the diffraction grating 59. The polychromator 41 serves as a beam splitter. A detector array 61 is located at a focal position of the concave mirror 60 at the output side of the polychromator 41 A spectrum of light reflected by the object can be measured by the detector array 61. The spectrum data measured by the detector array 61 is supplied to the analyzer 42 and is then analyzed therein. Operation control can be performed when an observer inputs a command from the man-machine interface 43 to the analyzer 42.

With the above arrangement, the observer inputs reflected light of a color belonging to a desired class while observing the object with the endoscope 40. This operation is repeated to prepare training sets, and the training sets are recorded in the analyzer 42. The internal arrangement of the analyzer 42 is identical to that of the processor 5 described with reference to the first embodiment. A spectral characteristic set Q and a transform matrix B are calculated in the same manner as in the first embodiment. A circuit for operating the transform matrix B is constituted as a matrix operation circuit 90. Spectral filters F1 to F5 for realizing the spectral character set Q are arranged.

A practical operation of this embodiment will be described below.

In preprocessing, an observer having knowledge for color classification inputs training sets of the respective classes by the apparatus shown in FIG. 12. This apparatus calculates spectral filter characteristics and the transform matrix B by statistic analysis. In this preprocessing for, e.g., a medical endoscope, a color of a normal tissue and colors of various morbid portions are analyzed to calculate the spectral filter characteristics and the transform matrix B. This preprocessing can be performed once. When an actual observation is to be performed, an observer manipulates the endoscope 70 while observing an image on a TV monitor 97. The observer then grasps color differences of the respective classes in accordance with a pseudo color display, as needed. If detailed analysis is required, the currently displayed image is frozen, and classification analysis and other measurements are performed.

According to the second embodiment, the functions of the present invention are applied to the image input apparatus to provide an arrangement suitable for color classification in an electronic endoscope. A pseudo color display is performed in an operation mode to obtain a normal color image without any discomfort and to emphasize differences between classes, thereby allowing the observer to effectively and visually grasp classification. Therefore, a diagnostic capability in medical applications and inspection capabilities in various industrial fields can be improved.

Setup conditions of the rotary filter 80, the matrix operation circuit 90, and the encoder 91 may be set variable to change the conditions in accordance with application purposes.

The third embodiment of the present invention will be described below. In this embodiment, color classification filters and an absolute color transform matrix are designed by an apparatus shown in FIG. 14, and actual measurements are performed by an apparatus shown in FIG. 15.

Figure 14:
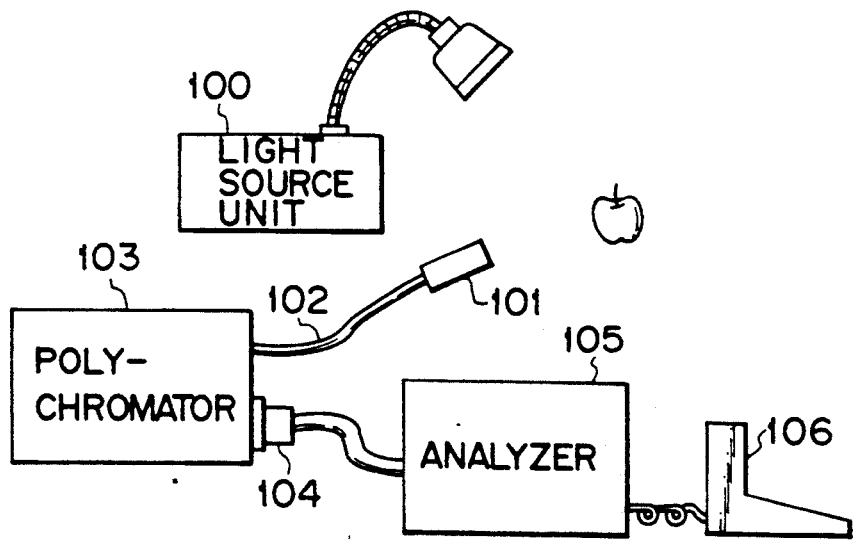
FIG. 14 is a block diagram showing a modification of the data generator.

A data generator shown in FIG. 14 comprises a light source unit 100, a polychromator 103 serving as a beam splitter for receiving reflected light from a light incident end 101 through a light guide 102, a detector array 104 for photoelectrically converting spectrum data of the reflected light split by the polychromator 103, an analyzer 105 for receiving spectrum data from the detector array 104 to perform predetermined arithmetic operations, and a man-machine interface 106 for inputting a command from the analyzer 105.

The light source unit 100 is arranged as an independent unit. The polychromator 103, the analyzer 105, and the man-machine interface 106 are identical to those in the second embodiment.

Training sets are generated and statistically analyzed by this data generator to form a set Q of l spectral characteristics and a transform matrix B. The data generation method of this embodiment is the same as that in the second embodiment.

Figure 15:
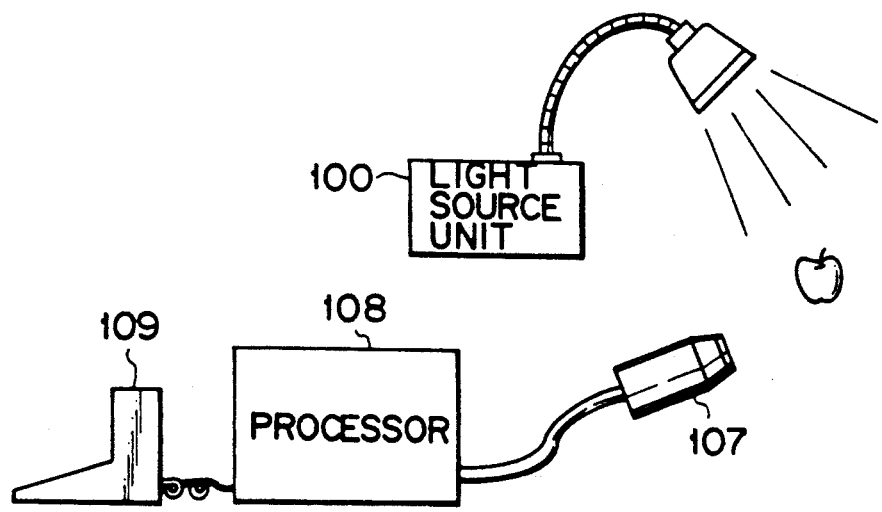
FIG. 15 is a schematic view showing an arrangement of a color discrimination apparatus according to the third embodiment of the present invention.

A color discrimination apparatus shown in FIG. 15 receives data associated with the color classification vectors generated by the data generator and data associated with the transform matrix B. The light source unit 100 in the color discrimination apparatus is identical to that shown in FIG. 14 and illuminates an object under the same conditions as in data generation.

Light reflected by the object is input to a detector head 107, and the detector head 107 detects intensities of light incident on l' ($l \geq 2l-1$) filters corresponding to the spectral characteristics constituting the set Q. The detected intensities are supplied to a processor 108.

The processor 108 has an arrangement identical to the processor described with reference to the first embodiment except that the static analysis processor and the liquid crystal filter driver I/F are omitted. The processor 108 performs classification and calculates the absolute colors in accordance with input signals from the detector head 107. The man-machine interface 109 is connected to the processor 108 and selects a desired operation mode of the observer and outputs operation results.

Figure 16A:
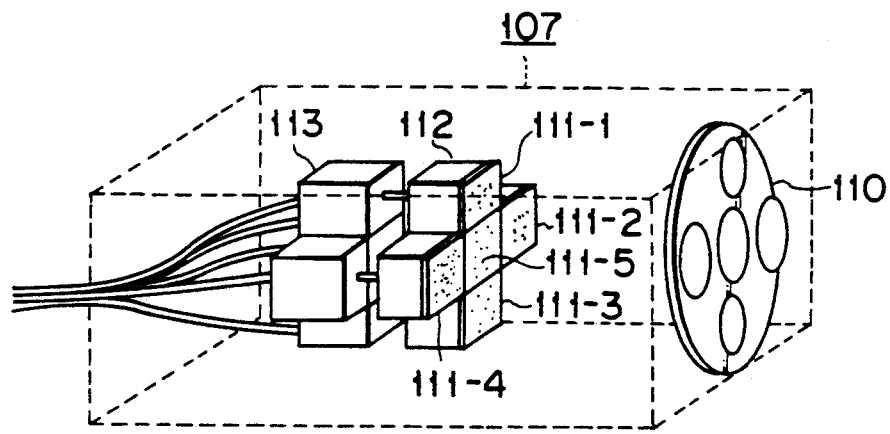
FIG. 16A is a view showing an arrangement of a detector head according to the third embodiment of the present invention.

FIG. 16A shows a structure of the detector head 107. In this embodiment, the number of spectral characteristics is given as $l = 3$, and the number of spectral filters is defined as $l' = 2l - 1 = 5$.

As shown in FIG. 16A, a lens array 110 having five lenses is located on the incident side of the detector head 107. A five-split photodetector 112 is located such that five photodetector elements are respectively located at focal points of the lenses of the lens array 110. Color filters 111-1 to 111-5 are adhered to the light-receiving surfaces of the photodetector elements, respectively. Each of the color filters 111-1 to 111-5 is constituted by bonding an interference filter, a color glass filter, and a Wratten filter, or by bonding several ones of these filters. The five color filters 111-1 to 111-5 have light-transmitting characteristics as spectral filter characteristics or characteristics close thereto. Intensities of light components transmitted through the color filters 111-1 to 111-5 are detected by photodetector elements of the photodetector 112 and are supplied to the processor 108 through corresponding amplifiers 113. The color filters 111-1 to 111-5 are constituted by $a_i$ color filters satisfying conditions of $d_i = d_i{}^{(1)} + \ldots d_i{}^{+(2)} + \ldots + d_i{}^{+(a_i)} + d_i{}^{-}(1) + d_i{}^{-}(2) + \ldots + d_i(a_i{}^{-1})$, $a_i = a_i{}^+ + a_i{}^-$, i.e., the classification vector $d_i$ ($i = 2, 3$) of the spectral characteristics of the set Q can be realized by two or more color filters.

According to this embodiment, since the plurality of color filters 111-1 to 111-5 having predetermined light-transmitting characteristics are arranged, it is effective to consider permanent use of a set of spectral filters. More specifically, data are generated beforehand by the apparatus described with reference to the second embodiment to set conditions for actual measurements. The color discrimination apparatus is very effectively used to repeat the same processing in a large quantity or for a long period of time while the characteristics of the color filters 111-1 to 111-5 and the numbers of photodetector elements of the photodetector 112 and the amplifiers 113 are kept unchanged. This embodiment is effective when color classification references of the objects are limited to a certain number, such as painting inspection on a mass-production line and color inspection of fresh meat, fish, and vegetables, thereby simplifying an apparatus arrangement.

Figure 16B:
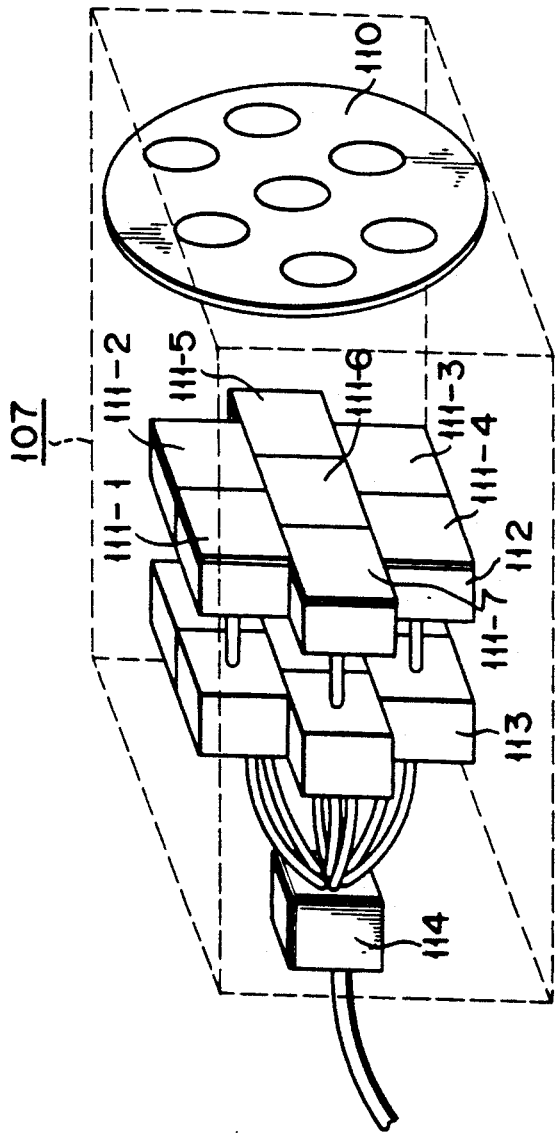
FIG. 16B is a view showing an arrangement of a detector head according to the fourth embodiment of the present invention.

The fourth embodiment of the present invention will be described below. FIG. 16B is a view showing a structure of a detector head 107 of this embodiment. This embodiment is different from the third embodiment in that color filters adhered to a photodetector 112 comprise a total of seven filters, i.e., color classification spectral filters 111-1 to 111-4 of the positive and negative characteristics $d_1{}^+$ and $d_2{}^+$, and $d_1{}^-$ and $d_2{}^-$ of the two color classification vectors $d_1$ and $\,_2$, and three primary color filters 111-5 to 111-7 for R, G, and B colors.

Intensities of light components transmitted through the seven filters 111-1 to 111-7 are amplified by photodetector elements of the photodetector 112. The amplified signals are selected as signals from the color classification filters 111-1 to 111-4 or the primary color filters 111-5 to 111-7 by a selector 114. The selected signal is supplied to a processor 108. Signal selection of the selector 114 is controlled by a control signal from the processor 108.

Each of the color classification filters of the color filters 111-1 to 111-7 may be constituted by $a_i$ ($a_i = a_i{}^+ + a_i{}^-$) filters as in the third embodiment. In this case, the number of lenses of the lens array 110, the number of photodetector elements of the photodetector 112, or the number of amplifiers 113 is set to be $a_1 + a_2 + 3$.

The same effect as in the third embodiment can be obtained in the fourth embodiment.

The fifth embodiment of the present invention will be described below.

A filter having a predetermined light-transmitting characteristic is arranged in a color discrimination apparatus as in the fourth embodiment, and a color image can be additionally displayed in the fifth embodiment.

Figure 17:
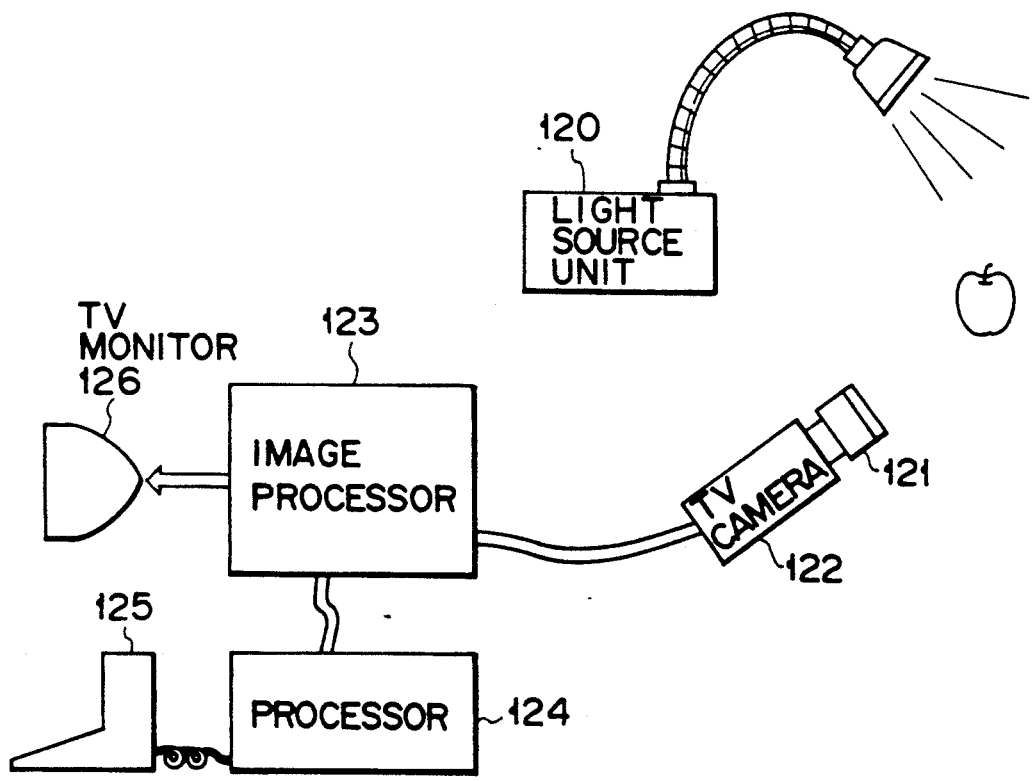
FIG. 17 is a view showing an arrangement of an image input/output apparatus according to the fifth embodiment of the present invention.

FIG. 17 is a view showing an arrangement of the fifth embodiment. This embodiment includes a light source unit 120, a photographic lens 121 for focusing light reflected by an object illuminated by the light source unit 120, a TV camera 122 for converting the reflected light incident on the photographic lens 121 into a video signal, an image processor 123 for converting the video signal output from the TV camera 122 into a color image signal, a processor 124 for performing predetermined processing of the data output from the image processor 123, and a man-machine interface 125 for inputting a command to the processor 124.

The light source unit 120 illuminates an object in the same conditions as in training set input at the time of data generation. An object image is focused by the photographic lens 121 and is input to the TV camera 122. An output signal from the TV camera 122 is input to the image processor 123. R, G, and B color image signals are output from the image processor 123 and are displayed as an image on the TV monitor 126.

On the other hand, image data input in accordance with the classification spectral characteristics are input from the image processor 123 to the processor 124 as needed and are analyzed by the processor 124. The observer can set an operation mode from the man-machine interface 125, and the processor 124 controls the overall apparatus operation.

FIG. 18 is a view showing the arrangement of the TV camera 122 and the image processor 123. The number of spectral filters calculated at the time of data generation is five, i.e., $\{\phi_1, d_1{}^+, d_1{}^-, \phi_2{}^+, d_2{}^-\}$.

A CCD image pickup device 131 is arranged in the TV camera 122. A plurality of light-receiving elements 132 are arranged in a matrix in the CCD image pickup device 131. The light-receiving elements 132 are connected to vertical shift registers 133, respectively, and each vertical shift register 133 is connected to a horizontal shift register 134. A color filter having a light-transmitting characteristic of each spectral filter is adhered to the light-receiving surface of each light-receiving element 132, as shown in FIG. 18.

Changes stored in the light-receiving elements 132 are shifted to the vertical shift registers 133 every other line within each field period and are then transferred to the horizontal shift register 134. The charges are output from the CCD image pickup device 122 through a buffer 135. An output from the CCD image pickup device 122 is input as a video signal to the image processor 123 through an amplifier 136. The video signal input to the image processor 123 is input to a CDS 141. The CDS 141 waveshapes the video signal. An output from the CDS 141 is input to one input terminal of a video amplifier 143 through a 1H-delay line 142, and an output from the CDS 141 is directly input to the other input terminal of the video amplifier 143. The video amplifier 143 calculates a difference between the video signal input through the 1H-delay line 142 and the video signal directly input from the CDS 141. More specifically, differences between the video signals (to be referred to as "+" signals hereinafter) from the color filters $d_1^+$, $d_2^+$, $\phi 1$, $d_1^+$, and $d_2^+$ of the light-receiving elements 132 and the video signals (to be referred to as "−" signals hereinafter) of the filters $d_1^-$, $d_2^-$, $\phi 1$, $d_1^-$, and $d_2^-$ of the light-receiving elements 132, so that signals of the spectral characteristics of $d_1 = d_1^+ - d_1^-$, $d_2 = d_2^+ - d_2^=$, O, $d_1$, $d_2$, ... are calculated. Subtractions from the "+" signals from the "−" signals are performed in the frame next to the frame within which the above operations are performed. In this case, a negative output signal is output from the video amplifier 143. For this reason, an analog switch 144 is arranged at the output terminal of the video amplifier 143. Of the video signals $d_1$, $d_2$, O, $d_1$, and $d_2$, the $d_1$ signal is sampled by sample/hold circuits 145 and 146, and the sampled signals are output to A/D converters 147 and 148, respectively. Outputs from the A/D converters 147 and 148 are recorded in frame memories 149 and 150, respectively.

Meanwhile, the output from the CDS 141 is directly sampled by a sample/hold circuit 151 and is recorded in a frame memory 153 through an A/D converter 152. The above operations are controlled by a system controller 154. The image signals representing the spectral characteristics of the vectors $d_1$, $d_2$, and $\phi_1$ recorded in the frame memories 149, 150, and 153 are subjected to the same processing as in the second embodiment and are output as R, G, and B color image signals by means of a matrix operation circuit 154, an encoder 155, multipliers 156 to 158, multipliers 159 to 161, a limiter 162, and a D/A converter 163, all of which are connected in the same manner as apparatus shown in FIG. 11.

An image displayed by the R, G, and B image signals is a real color image or an image in which differences between classes are emphasized by a pseudo color display in the same manner as in the second embodiment. A pseudo color gain is set by an observer at the man-machine interface 125 and is input to the multipliers 159 to 161 through the processor 124. Video signals recorded in the frame memories 149 and 150 are supplied to the processor 124 as needed, so that the processor 124 performs classification and image processing as needed.

The observer performs the following operation even in this embodiment. The observer observes a read color image or a pseudo color image on the TV monitor. An image is frozen as needed to perform classification of a local area of an image, classification of the entire image, or area calculations of classes.

The fifth embodiment is effective when a set of spectral filters are relatively permanently used as in the third embodiment, thereby simplifying the arrangement of the processor. In addition, since an object image can be dealt as a color image, the observer can more accurately grasp the object and simultaneously compare real tints of the object and classification in accordance with a real color display and a pseudo color display. Therefore, this embodiment is particularly effective for classification as in an endoscope of the second embodiment when an observer cannot directly observe an object.

The sixth embodiment of the present invention will be described below.

FIG. 19 shows an overall arrangement of an image input/output apparatus according to the sixth embodiment. This apparatus comprises a light source box 201 for emitting white light, a light source color generator 202 for converting white light generated by the light source box 201 into illumination light having a predetermined spectrum, a light guide 203 for guiding the illumination light output from the light source color generator 202 to an object 0, a TV camera 204, having a monochromatic image pickup device having a broad sensitivity characteristic for a visual light range or a wavelength range exceeding the visual light range, for receiving light reflected by the object O irradiated with the illumination light and for converting an image of the object O into an image signal, an image processor 205 for performing various processing operations such as visualization of color discrimination information for an image signal output from the TV camera 204, a processor 206 for controlling operations of the image processor 205 and the light source color generator 202, a data input unit 207 for inputting an operator's command to the processor 206, and a TV monitor 208 for displaying various types of images formed by the image processor 205.

The light source box 201 and the light source color generator 202 have the same arrangements as the light source box and the light source color generator shown in FIG. 2. When the constituting elements of the light source box 201 and the light source color generator 202 are to be described, the reference numerals in FIG. 2 are used. A liquid crystal filter 16 comprises color classification filters (positive and negative components) having spectral characteristics of the classification vectors $d_1$ and $d_2$ and the R, G, and B color image filters shown in FIG. 8.

Figure 20:
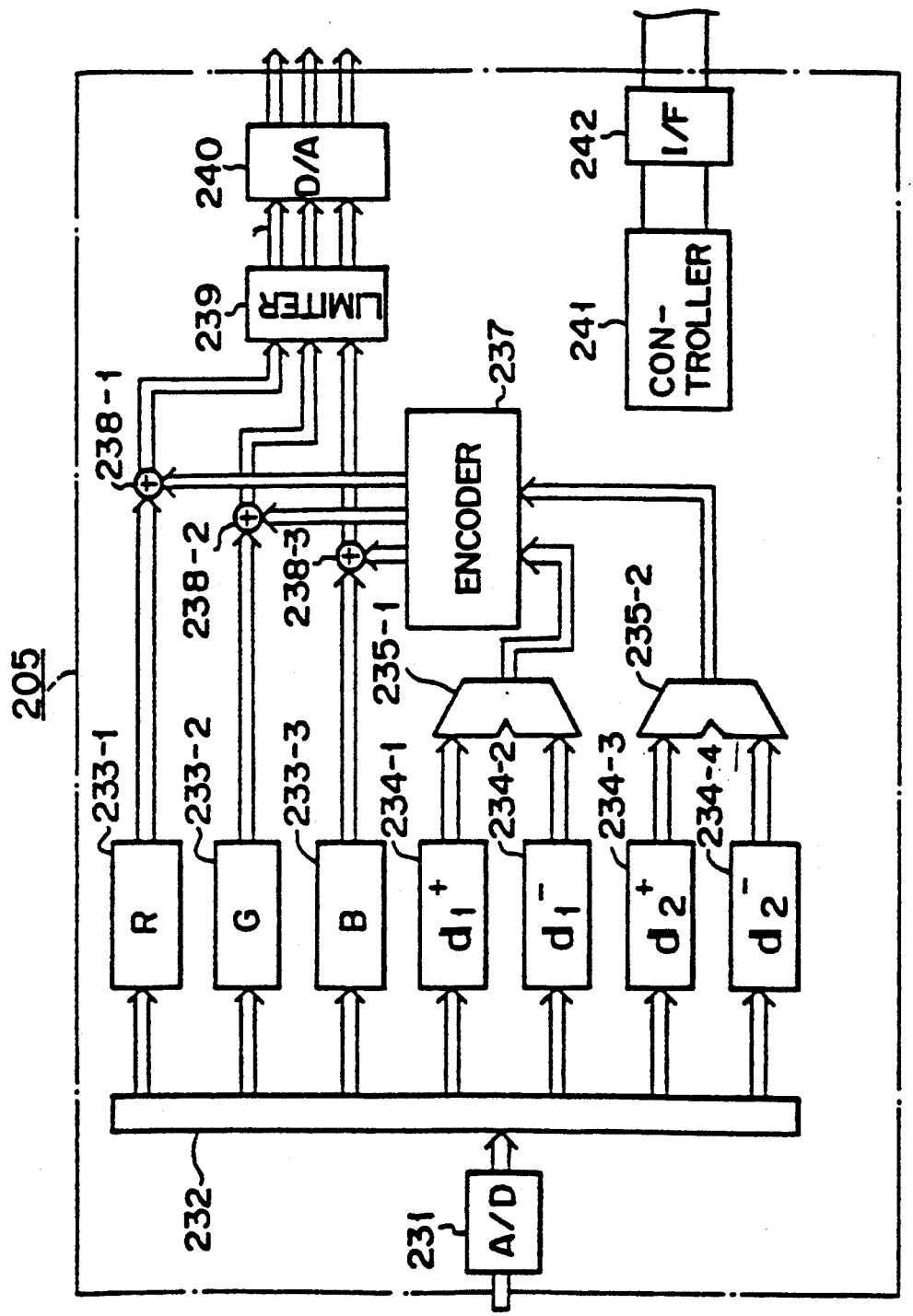
FIG. 20 is a view showing an arrangement of an image processor according to the sixth embodiment of the present invention.

An arrangement of the image processor 205 is shown in FIG. 20.

An image signal from the TV camera 204 is input to an A/D converter 231 in the image processor 205. The output terminal of the A/D converter 231 is connected to frame memories 233-1 to 233-3 corresponding to R, G, and B color image filters through a selector 232 and to frame memories 234-1 to 234-4 corresponding to the color classification filters. A digital image signal output from the A/D converter 231 is stored in the corresponding one of the frame memories which is designated by the selector 232. In this embodiment, there are two classification vectors for obtaining color classification filters, and each vector requires positive and negative characteristic filters. Therefore, there are four frame memories 234 respectively corresponding to the color classification filters. The frame memories 234-1 and 234-2 are connected to a subtracter 235-1, and the frame memories 234-3 and 234-4 are connected to a subtracter 235-2. The subtracters 235-1 and 235-2 calculate differences between input data from the frame memories 234-1 and 234-2 and from the frame memories 234-3 and 234-4, i.e., differences between the images. The two differences representing color discrimination information data are input to an encoder 237. The encoder 237 generates a predetermined coding signal for the R, G, and B signals on the basis of the color discrimination information of the color classification filter. The output terminal of the encoder 237 is connected to adders 238-1 to 238-3. The output terminals of the R, G, and B frame memories 233-1 to 233-3 are connected to these adders 238, respectively. The adders 238-1 to 238-3 add the color image signals stored in the R, G, and B frame memories 233-1 to 233-3 to the coding signals corresponding to the R, G, and B and output from the encoder 237, respectively, thereby obtaining an image signal containing color discrimination information. This image signal is input to a limiter 239, and subjected to appropriate overflow processing therein. An image signal output from the limiter 239 is input to a D/A converter 240. The D/A converter 240 converts the input data into R, G, and B analog video signals. These signals are output to the TV monitor 208.

The constituting components of the image processor 205 are controlled by a controller 241. The controller 241 is connected to the processor 206 through an interface 242. The controller 241 receives control signals representing operation menu selection and parameter setup from the processor 206.

The processor 206 comprises a personal computer and has an interface connected to the liquid crystal driver 16 and the controller 241. The processor 206 is also connected to the data input unit 207 such as a keyboard and also serves as a man-machine interface.

Color classification filters having optimal characteristics for specific color classification to be set in the liquid crystal filter 16 can be designed as in the first embodiment. In the first embodiment, the n-dimensional data is transformed into (r−1)-dimensional data to reduce the arithmetic operation volume so as to obtain the absolute color estimation matrix. Unlike the first embodiment, since this embodiment does not obtain any absolute color estimation matrix, the above operations are not performed. That is, in this embodiment, color discrimination information can be displayed as a color image without using any absolute color estimation matrix according to one of the characteristic features.

Each classification vector d has positive and negative components, as shown in FIG. 8. For this reason, each classification vector d is divided into positive and negative components, so that two filters, i.e., positive and negative component filters are arranged. Intensities of light components filtered through these positive and negative component filters must be subtracted as in the first embodiment.

In the embodiment having the above arrangement, white light generated by the light source box 201 is guided to the light source color generator 202, so that the magnitude of the incident light is adjusted by a slit 12. White light passing through the slit 12 is collimated again by a concave mirror 13, and the collimated light is guided to a diffraction grating 14. The first-order light diffracted by the diffraction grating 14 in a specific direction corresponding to a specific wavelength is reflected by a concave mirror 15, and the reflected light is focused on the liquid crystal filter 16.

The transmittance of the focusing position of the liquid crystal filter 16 at an arbitrary wavelength is adjusted by a liquid crystal filter driver 17 operated by the processor 206. For example, when spectrum data of an R wavelength range is to be extracted, transmittances of the focusing positions at other wavelengths are set small. Similarly, extraction can be performed in the G and B wavelength ranges. That is, the liquid crystal filter 16 serves as R, G, and B color image filters. In addition, the liquid crystal filter 16 also serves as four color classification filters on the basis of the respective components of the two classification vectors $d_1$ and $d_2$ in accordance with light-transmitting characteristics represented by the classification vectors d.

The characteristics of the R, G, and B color image filters and the characteristics of the color discrimination filters by the classification vectors d are set in the processor 206 beforehand. The transmittance distribution of the liquid crystal filter 16 is controlled on the basis of these characteristics, so that the liquid crystal filter driver 17 switches between the R, G, and B color image filters and the four color classification filters corresponding to the positive and negative components of the classification vectors $d_1$ and $d_2$.

The object O is sequentially irradiated with illumination light having wavelength regions of R, G, and B capable of generating a color image, and with illumination light of wavelength regions suitable for color classification.

On the other hand, the TV camera 204 converts light reflected by the object O irradiated with such illumination light into an image signal. This image signal is converted into a digital signal by the A/D converter 231 in the image processor 205, and the digital signals are stored in the frame memories 233-1 to 233-3 and 234-1 to 234-4 corresponding to the filters. Data obtained through a filter of a positive component of the classification vector $d_1$ is stored in the frame memory 234-1. Data obtained through a filter of a negative component of the classification vector $d_1$ is stored in the frame memory 234-2. Similarly, data obtained through filters of the positive and negative components of the vector $d_2$ are respectively stored in the frame memories 234-3 and 234-4. Data stored in the frame memories 234 corresponding to the color classification filters, i.e., both data from the frame memories 234-1 and 234-2 or both data from the frame memories 234-3 and 234-4 are input to a subtracter 235-1 or 235-2. The subtracter 235-1 or 235-2 calculates a difference between both the data to obtain color discrimination information of each classification vector. This color discrimination information is supplied to an encoder 237 as an output from the subtracter 235-1 or 235-2.

Since this color discrimination information does not contain color image information of R, G, and B, it must be converted into a predetermined encoded signal corresponding to the R, G, and B signals on the basis of the classification information of the color classification filters.

An operation of encoding the color discrimination information into R, G, and B signals will be described in detail below.

Assume that a measurement value by the classification vector $d_1$ is defined as $Z^1$, and that a measurement value by the classification vector $d_2$ is defined as $Z^2$. That is, the value $Z^1$ is a value of the difference between an image signal obtained by the positive component filter of the vector $d_1$ and the image signal from the negative component filter of the vector $d_1$. In a classification space {vector $d_1$, vector $d_2$}, a distribution of two colors is given, as shown in FIG. 8. The two classes are separated from each other using a line (to be referred to as a line L hereinafter) as a threshold reference represented by equation (58) below:

$$Z^2 = \partial Z^1 + \beta \tag{58}$$

Figure 21:
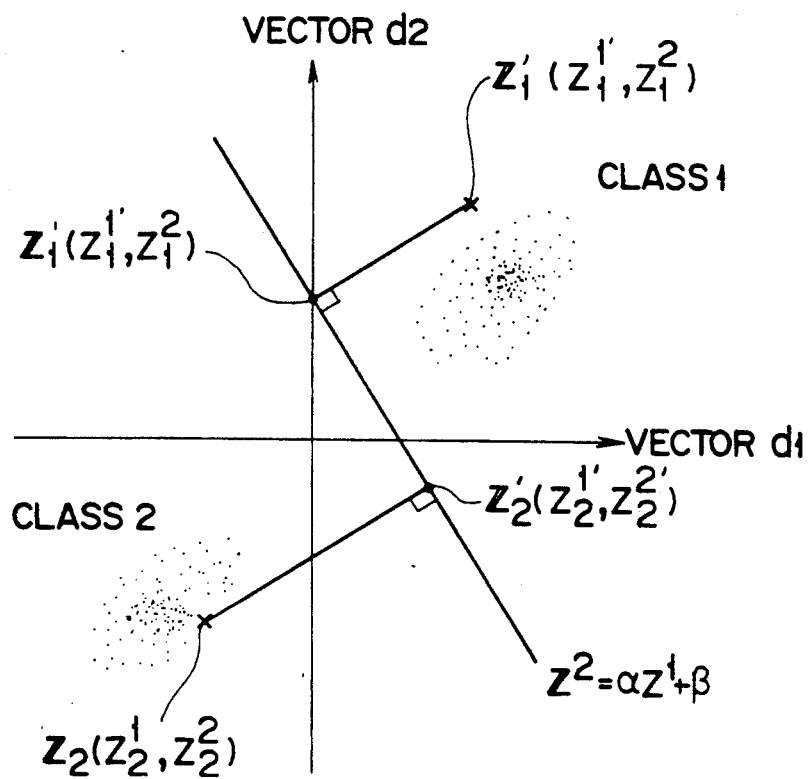
FIG. 21 is a graph showing classification results of measurement data according to the sixth embodiment of the present invention.

With this operation, a degree of separation between the classes can be represented by a geometric distance between the line L and a given measurement value vector $Z_1(Z_1^1, Z_1^2)$. That is, referring to FIG. 21, the measurement value vector $Z_1(Z_1^1, Z_1^2)$ is judged to belong to class 1, and its degree of separation can be expressed by a distance t1 between an intersection vector $Z_1$, between a normal from the vector $Z_1$ to the line L and the measurement value vector $Z_1$ as follows:

$$t1 = [(Z_1{}^1 - Z_1{}^{2'})^2 + (Z_1{}^2 - Z_1{}^{2'})^2]^{\frac{1}{2}} \quad (59)$$

$$Z_1{}^{1'} = \frac{Z_1{}^2 + 1/2 \cdot Z_1{}^1 - \beta}{\hat{e} + 1/2} \quad (59')$$

$$Z_1{}^{2'} = \frac{Z_1{}^2 + 1/2 \cdot Z_1{}^2 + \beta/\hat{e}^2}{1 + 1/\hat{e}^2}$$

When the measurement value vector Z is obtained, the intersection vector Z' set normal to the line L is calculated by equation (59). A correspondence between the measurement value vector and a class is determined in accordance with comparison of the calculated values. A degree t1 of separation is calculated by equation (59), and encoding is performed in accordance with equation (60).

$$\begin{bmatrix} R' \\ G' \\ B' \end{bmatrix} = \begin{bmatrix} R \\ G \\ B \end{bmatrix} + \gamma \begin{bmatrix} -S/2 \\ S \\ -S/2 \end{bmatrix} \quad (60)$$

where $\gamma$ is the transform constant. If $Z^1 \geq Z^{1'}$, then $S = t$; if $Z^1 < Z^1$, then $S = -t$. In this case, the transform constant $\gamma$ is appropriately determined in accordance with magnitudes of the original R, G, and B values.

Equation (60) is a case wherein color discrimination information is encoded to a G image. When the input vector is determined to belong to class 1, the image is more greenish, and a color complementary to green is weakened. However, when the input vector is determined to belong to class 2, the color complementary to green is increased. In this manner, tints of the green components can be expressed as differences between classes.

The above encoding is performed by the encoder 237 and the adders 238-1 to 238-3.

The R', G', and B' data obtained by the above encoding operation are converted into analog video signals by the D/A converter 240 through the limiter 239.

The TV monitor 208 processes the analog video signals output from the image processor 205 and displays a color image of the object O such that the color discrimination information represents, e.g., emphasized green. When the original R, G, and B images are not input, encoding is performed in accordance with equation (61):

$$\begin{bmatrix} R' \\ G' \\ B' \end{bmatrix} = \gamma \begin{bmatrix} O \\ S \\ O \end{bmatrix} (Z^1 \geq Z^{1'}) \quad (61)$$

$$\begin{bmatrix} R' \\ G' \\ B' \end{bmatrix} = \gamma \begin{bmatrix} S/2 \\ O \\ S/2 \end{bmatrix} (Z^1 < Z^{1'})$$

Since the R, G, and B image data stored in the frame memories 233-1 to 233-3 are not present, encoded signals output from the encoder 237 are converted into analog video signals.

In this embodiment, the image data of one object is read through the color classification filters suitable for specific color classification and the color image filters suitable for a color image input of R, G, and B. In addition, the color discrimination information as image data received through the color classification filters is converted into the encoded signals corresponding to the R, G, and B signals. Therefore, a color image of the object by R, G, and B can be displayed, and color discrimination information in the object image can also be visualized. Discrimination of a specific color which is difficult to be performed by the conventional R, G, and B filters can be performed. At the same time, matching with general color image equipment can be facilitated.

The seventh embodiment in which the sixth embodiment is applied to an electronic endoscope will be described below.

Figure 22:
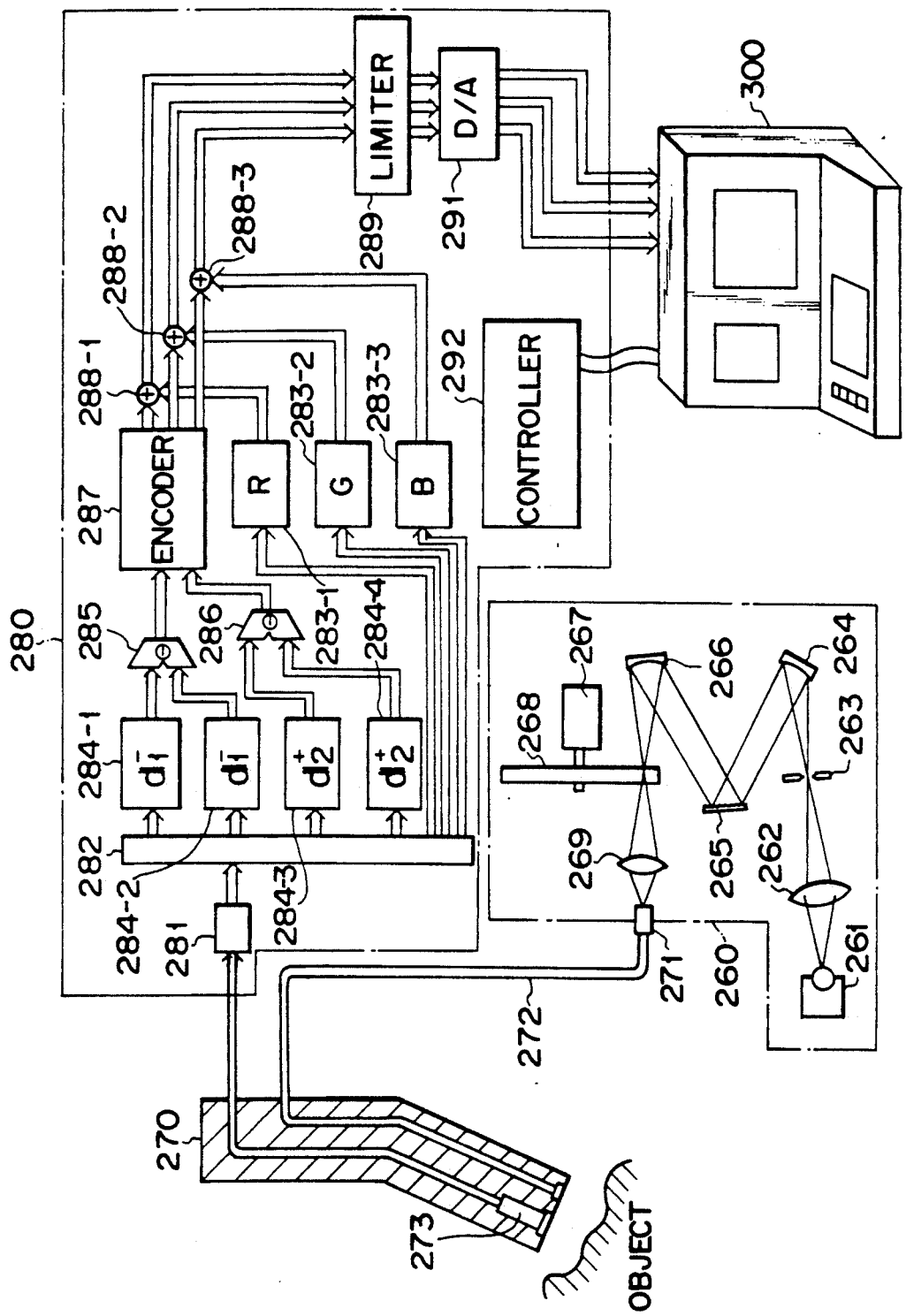
FIG. 22 is a view showing an internal structure of an electronic endoscope according to the seventh embodiment of the present invention.

FIG. 22 shows an overall arrangement of the seventh embodiment. This apparatus comprises a light source color generator 260, an endoscope probe 270 for illuminating a object with illumination light from the light source color generator 260, receiving light reflected by the object, and converting the reflected light into an image signal, an endoscope body 280, and a man-machine interface 300 for receiving an operator's command to the endoscope body 280 and displaying an image signal from the endoscope body 280.

In the light source color generator 260, illumination light emitted from white light lamp 261 passes through a lens 262 and a slit 263 located on the focal plane of the lens 262. The light is then collimated by a concave mirror 264, and the collimated light is input to a diffraction grating 265. The first-order light diffracted at a specific angle corresponding to a specific wavelength is focused on a concave mirror 266. A rotary filter 268 connected to a motor 267 rotated by a control means (not shown) is arranged on the focal plane of the concave mirror 266. Light passing through the rotary filter 268 is focused by a lens 269.

Figure 23A:
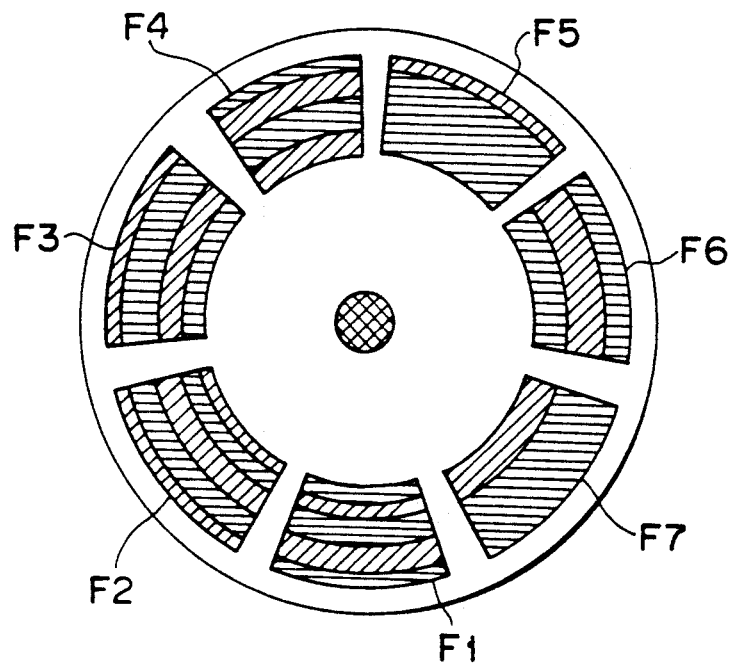
FIG. 23A is a plan view of a rotary filter used in the seventh embodiment of the present invention.

An arrangement of the rotary filter 268 is shown in FIG. 23A.

The rotary filter 268 comprises a total of seven filters, i.e., four color classification filters F1 to F4 comprising positive and negative component filters of the color classification vectors $d_1$ and $d_2$ suitable for specific color classification, and R, G, and B filters F5 to F7. These seven filters F1 to F7 are arranged in a rotational direction of the filter 268. Each of the filters F1 to F7 is realized by an ND filter having a transmittance distribution in accordance with predetermined spectral characteristics in the radial direction.

The rotary filter 269 is controlled to be rotated by one revolution per 30 seconds, i.e., a video rate by the motor 267. Therefore, seven illumination light components can be formed by the seven filters F1 to F7 within a one-frame period.

These illumination light components are incident on an incident-end connector 271 located at the rear focal plane of the lens 269. One end of a light guide 272 is connected to the connector 271, so that illumination light is guided to an endoscope 270 through the light guide 272. The respective illumination light components are sequentially incident on the object from the distal end of the endoscope probe 270 within the one-frame period. An endoscope camera 273 is arranged at the distal end of the endoscope probe 270. Images of the object illuminated with the respective illumination light components are picked up by the endoscope camera 273. Image signals thus obtained are input to the endoscope body 280.

In the endoscope body 280, the image signal from the endoscope probe 270 is input to an A/D converter 281. The output terminals of the A/D converter 281 are connected to R, G, and B image signal frame memories 283-1 to 283-3 and four color classification filter frame memories 284-1 to 284-4 through a selector 282. The selector 282 causes frame memories corresponding to the filters to store the corresponding image, e.g., causes the frame memory 283-1 to store an image of the object illuminated with the illumination light output from the R filter F5. The image signals input through the positive and negative component characteristic filters for the classification vector $d_1$ and stored in the frame memories 284-1 and 284-2 are input to a subtracter 285. Image signals input through the positive and negative component characteristic filters for the classification vector $d_2$ are input to a subtracter 286. Pieces of the color discrimination information of the classification vector d are obtained by the subtracters 285 and 286, respectively. These pieces of the color discrimination information obtained by the subtracters 285 and 286 and the R, G, and B image signals stored in the frame memories 283-1 to 283-3 are encoded into an image corresponding to the R, G, and B by means of an encoder 287 and adders 288-1 to 288-3 in the same manner as in the fifth embodiment. The encoded image in the manner described above is converted into an analog video signal through a limiter 289 and a D/A converter 291. A controller 292 is connected to a man machine interface 300 and controls the operation of the selector 282, encoding, and generation of the analog video signal.

An image of the object is displayed on a monitor screen of the man-machine interface 300 in accordance with a video signal from the endoscope body 280. When a normal color image is to be observed, only the R, G, and B image signals stored in the frame memories 283-1 to 283-3 are extracted and converted into video signals under the control of the controller 292, thereby displaying a normal color image on the monitor screen. When the color discrimination information is obtained from the image signals stored in the frame memories 284-1 to 284-4, and this color discrimination information is encoded into R, G, and B image signals, the color discrimination information associated with a specific color can be displayed in accordance with a pseudo color display mode. When the color discrimination information is encoded into R, G, and B image signals and the encoded results are added to the R, G, and B image signals stored in the frame memories 283-1 to 283-3, a color object image having visualized color discrimination information therein can be displayed. Therefore, a slight difference between colors of objects can be visually emphasized, and therefore color classification information of the object can be effectively grasped.

A modification of the light source color generator 260 according to the seventh embodiment will be described below.

Figure 23B:
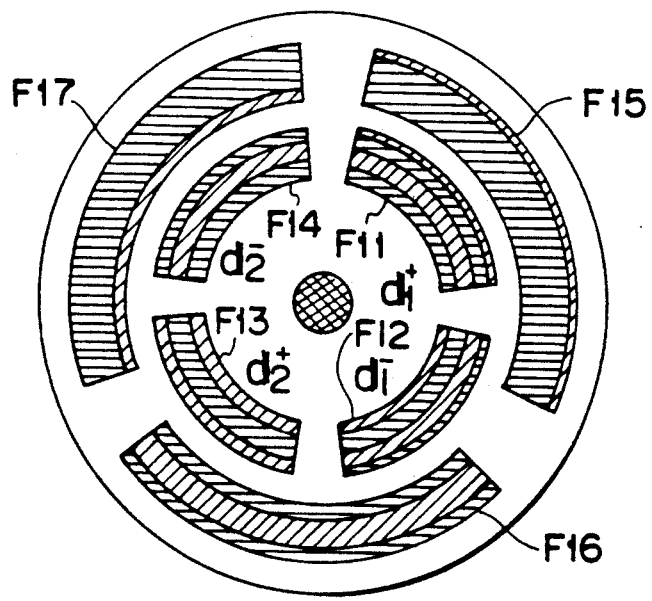
FIG. 23B is a view showing a modification of the rotary filter used in the seventh embodiment of the present invention.

This modification is obtained by changing a rotary filter and a motor portion for rotating the rotary filter. Other arrangements of this modification are the same as those of the seventh embodiment. An arrangement of the rotary filter of this modification is shown in FIG. 23B. This rotary filter 310 comprises a total of seven filters F11 to F17 having the same characteristics as those of the filters F1 to F7 arranged in the rotary filter 269. The filters F11 to F14 are color classification filters of the positive and negative components of the two classification vectors and are arranged in a rotational direction. The filters F15 to F17 are R, G, and B filters arranged outside the color classification filters F11 to F14.

Figure 24:
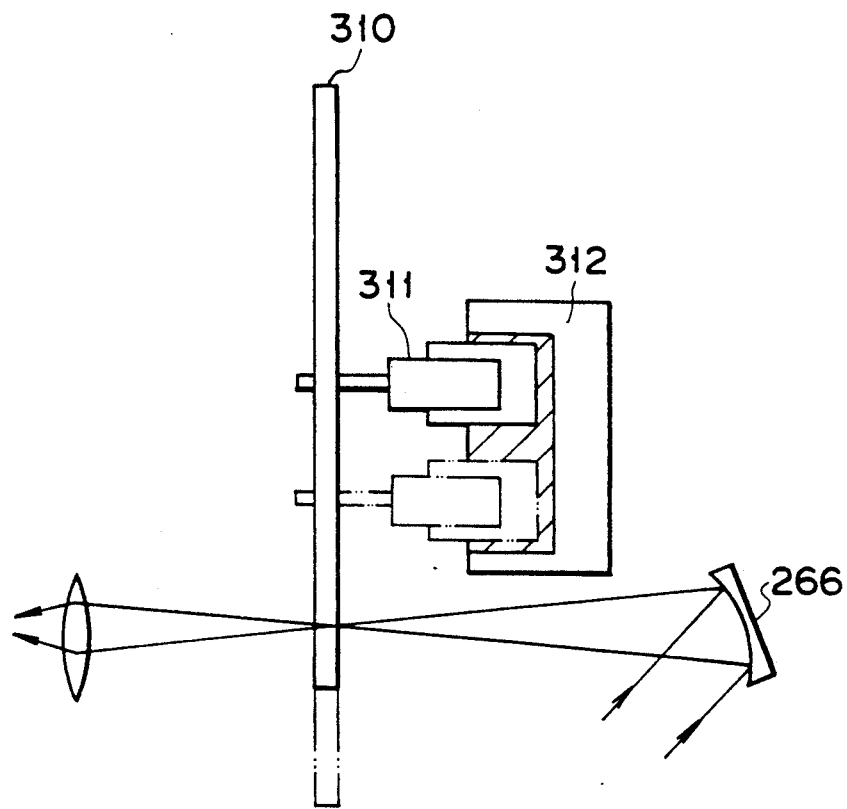
FIG. 24 is a view showing an arrangement of a motor used when the modification of the rotary filter shown in FIG. 23B is employed.

An arrangement of the motor portion is shown in FIG. 24.

A motor 311 for rotating the rotary filter 310 is supported on a motor support table 312. This motor support table 312 is slidably mounted on an apparatus body. The area of the outer filters F15 to F17 or the area of the inner filters F11 to F14 can be located at a focal position of the concave mirror 266. That is, upon movement of the rotary filter 310, the filters can be switched between the outer filters F15 to F17 and the inner filters F11 to F14.

In the modification having the above arrangement, the following three modes can be realized. The first mode is a color display mode for displaying a normal RGB image. This mode can be set by using the outer filters F15 to F17. Each of the primary color images (R, G, and B) is picked up within a period of 1/90 ($=(1/30) \times (\frac{1}{3})$) seconds, and the picked up image is stored in the corresponding frame memory.

The second mode is a pseudo color display mode using the color classification filters. When this mode is set, the four images obtained through the inner filters F11 to F14 of the rotary filter 310 are stored in the frame memories. In this case, each image is stored in the corresponding frame memory within a period of 1/120 ($=(1/30) \times \frac{1}{4}$) seconds. An output image is displayed by pseudo color encoding represented by equation (61) as described with reference to the sixth embodiment.

The third mode is a mode having the first and second modes. The R, G, and B filters F15 to F17 and the color classification filters F11 to F14 are switched every frame period, so that seven images through all the filters are obtained within a two-frame period. In this case, the image input timing is switched between 1/90 and 1/120 seconds every frame period. An output image is coded by equation (59) described with reference to the first embodiment. Therefore, the classification information is added to the color image, so that a semi-dynamic image updated every 1/15 ($=(1/30) \times 2$) seconds is displayed.

According to this modification, the image pickup time of each filter can be sufficiently obtained. An image having a high S/N ratio can be obtained, and the first to third modes can be arbitrarily selected. There is therefore provided an endoscope having a function of a conventional endoscope and a function of displaying a pseudo color image emphasizing a small difference in color between objects or displaying both the RGB color image and the pseudo display image in a superposed manner.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A color discrimination data input apparatus comprising:
    light source means for emitting an illumination light;
    spectroscope means for producing a spectrum including a plurality of spectral components from the illumination light emitted from said light source means;

color classification filter means having a spectrum characteristic that is usable for a classifying of objects and for an estimation of colors, said spectrum characteristic of said color classification filter means being set by means of a plurality of data samples of spectrums reflected from a plurality of objects to be classified into a plurality of classes, said color classification filter means including extracting means for extracting the plurality of spectral components from the spectrum generated by said spectroscope means;

illuminating means for illuminating a target object with said extracted spectral components extracted by said extracting means, such that reflected extracted spectral components are reflected by the target object, back to said color discrimination data input apparatus when the target object is illuminated by said illuminating means;

photoelectric converting means for converting the reflected extracted spectral components having a wavelength characteristic obtained by the spectrum passing through said color classification filter means, into an electrical signal;

computing means for color classifying the reflected extracted spectral components and for estimating a color of the target object, said computing means including:

color classifying means for classifying the reflected extracted spectral components into said plurality of classes in accordance with the electrical signal output from said photoelectric converting means; and color estimating means for estimating the color of the target object from the reflected extracted spectral components classified into any one of said plurality of classes by said color classifying means, by means of a preset absolute color estimation matrix; and output means for outputting a classification result obtained from said color classifying means and an object color measurement result output from said color estimating means.

2. An apparatus according to claim 1, wherein said color classification filter means has a light-transmitting characteristic which is determined by statistically constructing spectrum data from a training set prepared for each of the plurality of classes which include the reflected extracted spectral components.

3. An apparatus according to claim 1, wherein said color classification filter means comprises a liquid crystal filter whose transmittance is determined by liquid crystal alignment.

4. An apparatus according to claim 1, wherein said color estimating means includes means for estimating three primary color components of the reflected extracted spectral components according to a light-transmitting characteristic of said color classification filter means and color matching functions of three primary colors.

5. An apparatus according to claim 1, wherein said output means includes means for displaying the classification result in a pseudo color and displaying the object color measurement result as a color image.

6. An apparatus according to claim 2, further comprising a data generator including:

means for constructing the training set comprising the plurality of classes from the reflected extracted spectral components, obtained by illuminating a plurality of samples, the classes of each of the reflected extracted spectral components of which is known;

means for transforming the training set into a training set having lower dimensional degrees in unit of classes, by projecting the training set of each of the classes into a space constituted by r eigenvectors obtained by a major component analysis, the space being a space U complementarily orthogonal to a first major component vector, and the major component analysis operating a calculation of interclass covariance matrix from the training set of a reference class in the classes which correspond to a reference color;

means for calculating a vector for maximizing a Fisher ratio representing a degree of separation between the classes from the training sets having the lower dimensional degrees;

setting means for setting the light-transmitting characteristic of said color classification filter means on the basis of the vector; and means for calculating the absolute color estimation matrix corresponding to the light-transmitting characteristic set by said setting means and color matching functions of three primary colors.

7. An apparatus according to claim 1, wherein said color classification filter means includes a plurality of filters by which light-transmitting characteristics are obtained, and said color estimating means includes a matrix operation circuit means for operating the absolute color estimation matrix.

8. An apparatus according to claim 7, wherein said photoelectric converting means comprises an image detector, and said apparatus further includes:

A/D converting means for converting the electrical signal output from said photoelectric converting means into reflected extracted spectral component data constituted by a digital signal; and a plurality of frame memories, arranged in correspondence with said plurality of filters, each of said frame memories storing reflected extracted spectral component data input through the corresponding one of said filters, and the reflected extracted spectral component data read out from said plurality of frame memories being input to said matrix operation circuit means and said color classifying means.

9. An apparatus according to claim 1, wherein said photoelectric converting means includes image pickup means for converting the reflected spectral components from the target object into an image signal.

10. A color discrimination data input apparatus comprising:

light source means for emitting an illumination light;

spectroscope means for producing a spectrum including a plurality of spectral components from the illumination light emitted from said light source means;

color classification filter means having a spectrum characteristic that is usable for a classifying of objects and for an estimation of colors, said spectrum characteristic of said color classification filter means being set by means of a plurality of data samples of spectrums reflected from a plurality of objects to be classified into a plurality of classes, said color classification filter means including extracting means for extracting the spectral components from the spectrum generated by said spectroscope means;

illuminating means for illuminating a target object with said extracted spectral components extracted by said extracting means, such that reflected extracted spectral components are reflected by the target object, back to said color discrimination data input apparatus when the target object is illuminated by said illuminating means;

a color filter having a light-transmitting characteristic suitable for input of a color image of three primary colors thereto;

image pickup means for converting the reflected extracted spectral components from the target object, into an image signal;

photoelectric converting means for converting the reflected extracted spectral components having a wavelength characteristic obtained by the spectrum passing through said color classification filter means, into an electrical signal; and filter control means for selectively locating said color classification filter means and said color filter in an optical path between said light source means and said photoelectric converting means as needed.

11. An apparatus according to claim 10, further comprising image forming means for encoding the image signal from said image pickup means, upon insertion of at least said color classification filter means in the optical path, into three primary colors on the basis of a light-transmitting characteristic of said color classification filter means to form an image as visualized color discrimination information contained in the image signal.

12. An apparatus according to claim 11, wherein said image forming means includes means for forming a color image from the image signal from said image pickup means and a color image obtained by superposing the color discrimination information on the color image upon insertion of said color filter in the optical path.

13. An apparatus according to claim 10, wherein said color classification filter means comprises a liquid crystal filter whose transmittance is determined by liquid crystal alignment.

14. An apparatus according to claim 11, wherein said color classification filter means includes a plurality of filters by which the light-transmitting characteristics are obtained.

15. An apparatus according to claim 14, wherein said image forming means includes:

A/D converting means for converting an image signal output from said image pickup means into reflected spectral component data including a digital signal;

a plurality of frame memories arranged in correspondence with said plurality of filters and said color filter, each of said frame memories storing reflected spectral component data input through the corresponding one of said filters;

a coding circuit for coding the reflected spectral component data read out from said plurality of frame memories into signals corresponding to R, G and B signals in accordance with the light-transmitting characteristic of the color classification filter means; and an adder means for adding the reflected spectral component data read out from said plurality of frame memories corresponding to said color filter to coded signal output from said coding circuit in unit of color components, and for generating an image signal containing the color discrimination information.

* * * * *